(12) United States Patent
Kanazawa et al.

(10) Patent No.: US 9,457,084 B2
(45) Date of Patent: Oct. 4, 2016

(54) USE OF EP4 RECEPTOR ANTAGONISTS IN THE TREATMENT OF IL-23 MEDIATED DISEASES

(75) Inventors: Kiyoshi Kanazawa, Aichi (JP); Kazuhiko Nonomura, Shizuoka (JP); Takako Okumura, Aichi (JP); Shinichi Koizumi, Aichi (JP)

(73) Assignee: RAQUALIA PHARMA INC., Aichi (JP)

( * ) Notice: Subject to any disclaimer, the term of this patent is extended or adjusted under 35 U.S.C. 154(b) by 404 days.

(21) Appl. No.: 13/580,323

(22) PCT Filed: Feb. 22, 2011

(86) PCT No.: PCT/JP2011/000994
§ 371 (c)(1),
(2), (4) Date: Aug. 30, 2012

(87) PCT Pub. No.: WO2011/102149
PCT Pub. Date: Aug. 25, 2011

(65) Prior Publication Data
US 2012/0316197 A1 Dec. 13, 2012

Related U.S. Application Data

(60) Provisional application No. 61/682,506, filed on Feb. 22, 2010.

(51) Int. Cl.
A01N 43/42 (2006.01)
A61K 31/44 (2006.01)
(Continued)

(52) U.S. Cl.
CPC ............... A61K 45/06 (2013.01); A61K 31/38 (2013.01); A61K 31/437 (2013.01); A61K 31/44 (2013.01); A61K 31/443 (2013.01); A61K 31/4412 (2013.01)

(58) Field of Classification Search
USPC ....... 514/303, 336, 355, 382, 394, 444, 448, 514/563; 546/118, 284.7, 316; 548/253, 548/304.4; 549/60, 72; 562/451
See application file for complete search history.

(56) References Cited

U.S. PATENT DOCUMENTS 6,710,054 B2  3/2004  Nakao et al.
7,238,714 B2  7/2007  Nakao et al.
(Continued)

FOREIGN PATENT DOCUMENTS

JP  2004-517054 A  6/2004
JP  2006-516600 A  7/2006
(Continued)

OTHER PUBLICATIONS

Lofberg et al. (Aliment Pharmacol Ther 1993, 7, 611-616).*
(Continued)

Primary Examiner — Uma Ramachandran
(74) Attorney, Agent, or Firm — Marshall, Gerstein & Borun LLP

(57) ABSTRACT

This invention relates to a compound with EP4 antagonistic activity, or a pharmaceutically acceptable salt with EP4 receptor antagonistic activities, which is useful in the treatment of immune disease or allergy. This invention also relates to a compound of formula (I), (II), (III), (IV), (Va) or (Vb), or a pharmaceutically acceptable salt thereof with EP4 receptor antagonistic activities, which is useful in the treatment of immune disease or allergy. This invention also relates to a pharmaceutical composition for the treatment of immune disease or allergy which comprises a therapeutically effective amount of a compound of formula (I), (II), (III), (IV), (Va) or (Vb), or a pharmaceutically acceptable salt thereof. Further this invention relates to a method for the treatment of immune disease or allergy in an animal subject including a mammalian subject, which comprises administering to the animal subject including a mammalian subject a compound of the formula (I), (II), (III), (IV), (Va) or (Vb), or a pharmaceutically acceptable salt thereof.

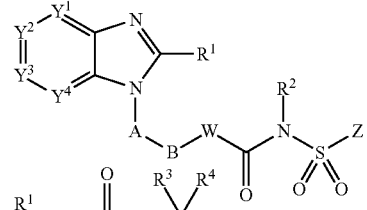

(I)

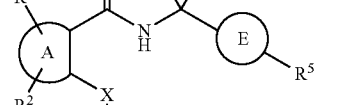

(II)

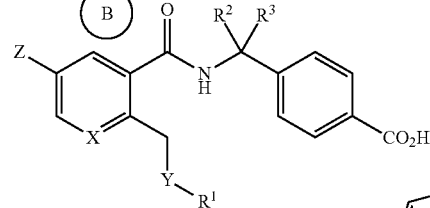

(III)

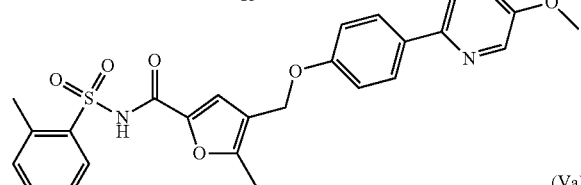

(IV)

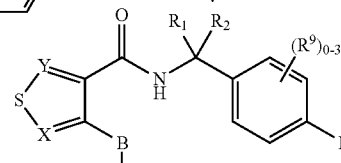

(Va)

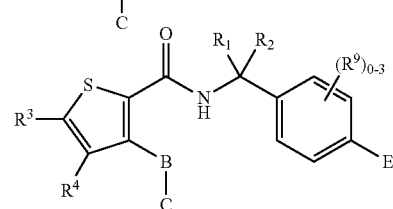

(Vb)

1 Claim, 2 Drawing Sheets

(51) Int. Cl.

| | |
|---|---|
| A01N 37/12 | (2006.01) |
| A01N 47/28 | (2006.01) |
| A61K 31/17 | (2006.01) |
| C07D 513/02 | (2006.01) |
| C07D 515/02 | (2006.01) |
| C07D 211/72 | (2006.01) |
| A61K 45/06 | (2006.01) |
| A61K 31/38 | (2006.01) |
| A61K 31/437 | (2006.01) |
| A61K 31/4412 | (2006.01) |
| A61K 31/443 | (2006.01) |

(56) References Cited

U.S. PATENT DOCUMENTS

| | | | |
|---|---|---|---|
| 7,534,914 B2 | 5/2009 | Koike et al. | |
| 2004/0192767 A1 | 9/2004 | Oxford et al. | |
| 2005/0065188 A1* | 3/2005 | Nakao | C04B 35/632 |
| | | | 514/341 |
| 2009/0247596 A1 | 10/2009 | Blouin et al. | |

FOREIGN PATENT DOCUMENTS

| | | |
|---|---|---|
| JP | 2007-504210 A | 3/2007 |
| JP | 2007-536366 A | 12/2007 |
| JP | 2010-500293 A | 1/2010 |
| WO | WO-03086371 A2 | 10/2003 |
| WO | WO-2006095268 A1 | 9/2006 |

OTHER PUBLICATIONS

Sheridan (J. Chem. Inf. Comput. Sci., 2002, vol. 42, pp. 103-108).*
Reimold (J Postgrad Med 2005, 51, 273).*
Takaoko Okumura, et al. "Effects of the selective $EP_4$ antagonist, CJ-023, 423 on chronic inflammation and bone destruction in rat adjuvant-induced arthritis", Journal of Pharmacy and Pharmacology, pp. 723-730 (2008).
S.N.S. Murthy, et al. "Beneficial effect of MDL 73404 in dextran sulfate-mediated murine colitis", Agents Actions 41, Special Conference Issue, C233-234 (1994).
Hiroshi Keino et al., "Therapeutic effect of the potent IL-12/IL-23 inhibitor STA-5326 on experimental autoimmune uveoretinitis", Arthritis Research & Therapy, pp. 1-8, (2008).
Supplementary European Search Report from corresponding EP 11744440, dated Sep. 2, 2013, 5 pages.
International Preliminary Report on Patentability in corresponding PCT/JP2011/000994 dated Aug. 28, 2012.
International Search Report in corresponding PCT/JP2011/000994 mailed Mar. 29, 2011.
Written Opinion in corresponding PCT/JP2011/000994 mailed Mar. 29, 2011.
Yao et al., "Prostaglandin E2-EP4 signaling promotes immune inflammation through TH1 cell differentiation and TH17 cell expansion," Nature Medicine 15(6); 633-640, 2009.
Chen et al., "A novel antagonist of the prostaglandin E2EP4 receptor inhibits Th1 differentiation and Th17 expansion and is orally active in arthritis models," British Journal of Pharmacology 160(2); 292-310, 2010.
Negishi et al., "Molecular mechanisms of diverse actions of prostanoid receptors," Biochemica et Biophisica Acta 1259: 109-120, 1995.
Betelli et al., "TH-17 cells in the circle of immunity and autoimmunity," Nature Immunology 8(4):345-350, 2007.
Fossiez et al., "Interleukin-17," Intern. Rev. Immunol. 16; 541-551, 1998.
Jovanovic et al., "IL-17 Stimulates the Production and Expression of Proinfalmmatory Cytokines, IL-β and TNF-α by Human Macrophages," J. Immunol. 160: 3513-3521, 1998.

Ito et al., "Involvement of IL-17A in the pathogenesis of DSS-indiced colitis in mice," Biochemical and Biophysical Research Communications 377:12-16, 2008.
Komiyama et al., "IL-17 Plays and Important Role in the Development of Experimental Autoimmune Encephalomyelitis," J. Immunol. 177:566-573, 2006.
Fujino et al., "Increased expression of interleukin 17 in inflammatory bowel disease, " Gut 52:65-70, 2003.
Tzartos, et al., "Interleukin-17 Production in Central Nervous System-Infiltrating T Cells and Glial Cells Is Associated with Active Disease in Multiple Sclerosis," The American Journal of Pathology 172:146-155, Jan. 2008.
Caproni et al., "Serum Levels of IL-17 and IL-22 Are Reduced by Etanercept, but not by Acitretin, in Patients with Psoriasis: a Randomized-Controlled Trial, " J. Clin. Immunol. 29:210-214, 2009.
Kotake et al., "IL-17 in synovial fluids from patients with rheumatoid arthritis is a potent stimulator of osteoclastogenesis," The Journal of Clinical Investigation 103(9):1345-1353, May 1999.
Oppmann et al., "Novel p 19 Protein Engages IL-12p40 to Form a Cytokine, IL-23, with Biological Activities Similar as Well as Distinct from IL-12," Immunity 13:715-725:715-725, Nov. 2000.
Wiekowski et al., "Ubiquitous Transgenic Expression of the IL-23 Subunit p19 Induces Multiorgan Inflammation, Runting, Infertility, and Premature Death," The Journal of Immunology 166: 7563-7570, 2001.
Aggarwal et al.,"Interleukin-23 Promotes a Distinct CD4T Cell Activation state Characterized by the Production of Interleukin-17 ," J. Biol. Chem. 278(3) 1910-1914, 2003.
Cua et al., "Interleukin-23 rather than interleukin-12 is the critical cytokine for autoimmune inflammation of the brain," Nature 421 :744-748, 2003.
Murphy et al., Divergent Pro- and Antiinflammatory Roles for IL-23 and IL-12 in Joint Autoimmune Inflammation, J. Exp. Med 198:1951-1957, 2003.
Yen et al., "IL-23 is essential for T cell-mediated colitis and promotes inflammation via IL-17 and IL-6," J. Clin. Invest. 16(5):1310-1316, 2006.
Sandborn, et al., "A Randomized Trial of Ustekinumab, a Human Interleukin—12/23 Monoclonal Antibody, in Patients with Moderate-to-Severe Chrohn's Disease," Gastroenterology 135:1130-1141, 2008.
Krueger et al., "A Human Interleukin—12/23 Monoclonal Antibody for the Treatment of Psoriasis," N Engl J Med 356(6): 580-592, 2007.
Steinman, L., "A brief history of TH17, the first major revision in the TH1/TH2 hypothesis of T cell-mediated tissue damage," Nat Med 13: 139-145, 2007.
Wong et al., "Elevation of proinflammatoryu cytokine (IL-18, IL__17, IL-12) and Th2 cytokine (IL-4_concentrations in patients with systemic lupus erythematosus," Lupus 9:589-593, 2000.
Albanesi et al., "IL-17 Is Produced by Nickel-Specific T Lymphocytes and regulates ICAM-1 Expression and Chemokine Production in Human Keratinocytes: Synergistic or Antagonist Effects with IFN-γ and TNF-α," J Immunol 162:494-502, 1999.
Nakae et al., "Antigen-Specific T Cell Sensitization Is Imparied in IL-17 Deficient Mice, causing Suppression of Allergic Cellular and Humoral Responses," Immunity 17: 375-387, Sep. 2002.
Kabashima et al., "Prostaglandin E2-EP4 signaling initiates skin immune responses by promoting migration and maturation of Langerhans cells," Nat Med 9(6): 744-749, Jun. 2003.
Kabashima et al., "The prostaglandin receptor EP4 suppresses colitis, mucosal damage and CD4 cell activation in the gut," J Clin Invest 109(7):883-893, Apr. 2002.
Honda M et al., "Prostaglandin E2-EP3 signaling suppresses skin inflammation in murine contact hypersensitivity," J Allergy Clin Immunol 124: 809-818, 2009.
European Office Action for Application No. 11 744 440.6-1464, dated Apr. 30, 2014.

* cited by examiner

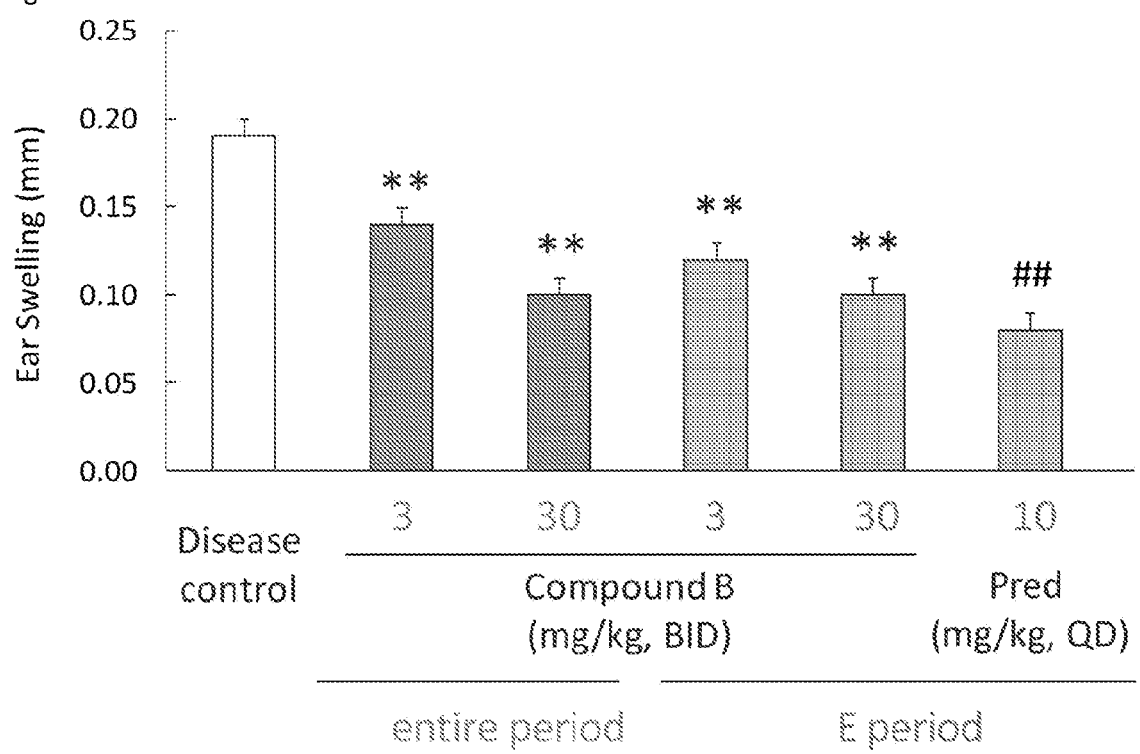

USE OF EP4 RECEPTOR ANTAGONISTS IN THE TREATMENT OF IL-23 MEDIATED DISEASES

TECHNICAL FIELD

This invention relates to compounds for use in therapeutic treatment of the human body. In particular, it relates to compounds with selective EP4 receptor antagonism which are useful for treating immune disease or allergy, or preventing or delaying the onset or the progression of immune disease or allergy.

This invention also relates to a pharmaceutical composition for the treatment of immune disease which comprises a therapeutically effective amount of a compound of formula (I), (II), (III), (IV), (Va) or (Vb), or a pharmaceutically acceptable salt thereof. This invention relates to a method for the treatment of immune disease in an animal subject including a mammalian subject, which comprises administering to the animal subject including a mammalian subject a compound of the formula (I), (II), (III), (IV), (Va) or (Vb), or a pharmaceutically acceptable salt thereof. Further this invention relates to a method for the treatment of immune disease or allergy in an animal subject including a mammalian subject, which comprises administering to the animal subject including a mammalian subject in need a therapeutically effective amount of a compound of the formula (I), (II), (III), (IV), (Va) or (Vb), or a pharmaceutically acceptable salt thereof.

BACKGROUND ART

Prostaglandin E2 (PGE2) is a potent modulator involved in the pathogenesis of a variety of diseases such as inflammation, pain, arthritis, and cancer. PGE2 binds to at least four subtypes of PGE receptor, designated EP1, EP2, EP3, and EP4. Molecular pharmacology studies have revealed that all subtypes are 7-transmembrane spanning receptors that belong to the G-protein coupled receptor superfamily. EP1 activation stimulates the release of intracellular calcium; EP2 and EP4 stimulation both activate adenylate cyclase but differ in their response to certain ligands; and EP3 stimulation inhibits adenylate cyclase via inhibitory G-proteins (NPL 1).

Two distinct types of helper T (Th) cells, Th1 and Th2 cells, were discovered in 1986. Th1 cells are characterized by production of IFN-gamma and are thought to be crucial for the development of autoimmune diseases. On the other hand, Th2 cells are characterized by production of Interleukin (IL)-4 and are thought to play important roles in allergic diseases. Recently, a third subset of Th cell, called Th17 cells, was discovered and Th17 cells are characterized by production of a proinflammatory cytokine IL-17 (NPL 2). IL-17 has potent in inducing inflammatory cytokines such as TNF-alpha and IL-6 on various types of cells (NPL 3; NPL 4). It has been shown that IL-17-deficient mice are resistant to IBD and multiple sclerosis (MS) (NPL 5; NPL 6). Induction of IL-17 level in the serum and disease tissues has been detected in the patients with IBD, MS, psoriasis, and rheumatoid arthritis (NPL 7; NPL 8; NPL 9; NPL 10). These data suggest the involvement of Th17 cells in the development of various human autoimmune diseases and allergy.

Interleukin (IL)-23 is a heterodimeric molecule composed of p40 and p19 (NPL 11). Transgenic p19 overexpressing mice die before the age of 3 months following systemic inflammation, which indicates a prominent pro-inflammatory role for IL-23 (NPL 12). It has been demonstrated that IL-23 is important for expansion of Th17 cells in vitro (NPL 13). Mice lacking p19 were resistant to collagen-induced arthritis, experimental autoimmune encephalomyelitis and inflammatory bowel disease, because the generation of Th17 cells is impaired in the absence of IL-23 (NPL 14; NPL 15; NPL 16). In animal model and human, both IL-23 and IL-17 have been demonstrated to play important roles in many autoimmune diseases. For example, increases amounts of IL-23 have been associated with IBD, rheumatoid arthritis and psoriasis in human. And an anti-p40 antibody which neutralizes the effect of IL-23 demonstrates clinical efficacy in patients with IBD and psoriasis (NPL 17; NPL 18). These evidences suggest that IL-23 is important for the function of Th17 cells as well as the pathogenesis of autoimmune diseases.

AE3-208 is an EP4 antagonist which is generally used in non-clinical research experiments. AE3-208 was demonstrated to ameliorate MS and allergic contact dermatitis in animal models (NPL 19).

Autoimmune diseases develop when the patient's immune system is activated against substances and tissues normally present in the body. The pathogenesis of autoimmune diseases has yet to be clearly defined. Although the emergence of biological agents such as anti-TNF alpha antibody has greatly improved some kinds of autoimmune diseases, these agents are expensive and have risks of significant side effects. Therefore, a small-molecule medicine for autoimmune diseases is anticipated. Recent studies suggest that Th17, or both Th1 and Th17 mediate autoimmune diseases such as IBD, MS, RA, and psoriasis (NPL 20). Furthermore, PGE2-EP4 signaling has been demonstrated to promote immune diseases through Th1 and Th17 cells. EP4 antagonist (AE3-208) was demonstrated to restore immune systems and treat MS in mice (NPL 21).

The allergic disorder is a genetically and environmentally affected multifactorial disease. While the etiology of allergy has not been fully understood, IL-17 has been reported to play crucial roles in allergy. Induction of IL-17 was found in the sera of allergic asthma patients and of allergic contact dermatitis (NPL 22 and NPL 23). In addition, IL-17 deficient mice are resistant to cause allergic asthma and allergic contact dermatitis (NPL 24). Above evidences strongly suggest the close relationship of IL-17 as well as Th17 in the causative mechanism of allergy.

Moreover, the potential of EP4 antagonism in the therapy of some kinds of allergy was validated using AE3-208. AE3-208 showed potent inhibitory efficacy on the development (sensitization) in mice allergic contact dermatitis model (NPL 25). These data suggest that EP4 antagonism will be a potential mechanism for the prophylactic drug of allergy. However, AE3-208 failed to show the efficacy by therapeutic treatment in this study. In terms of the clinical value of the drugs in this area, drugs which are available in the therapeutic stage are highly valuable than drugs whose usage is limited in the prophylactic use. Even worse, AE3-208 aggravated rat in DSS (dextran sodium sulfate)-induced colitis model, an IBD model.

In addition, nonsteroidal anti-inflammatory drugs such as indomethacin, which may have similar immune mechanism to EP4 antagonist, also aggravated DSS-induced colitis (NPL 26), and make allergic contact dermatitis worse in contact hypersensitivity model (NPL 27).

CITATION LIST

Non Patent Literature

NPL 1: Biochim Biophys Acta 1259: 109-19, 1995
NPL 2: Nat. Immunol. 8: 345-350, 2007

NPL 3: Int Rev Immunol. 16: 541-551, 1998
NPL 4: J. Immunol. 160: 3513-3521, 1998
NPL 5: Biochem Biophys Res Commun. 377:12-16, 2008
NPL 6: J. Immunol. 177:566-573, 2006
NPL 7: Gut 52:65-70, 2003
NPL 8: Am J Pathol. 172:146-155, 2008
NPL 9: J Clin Immunol. 29:210-214, 2009
NPL 10: J Clin Invest. 103:1345-1352, 1999
NPL 11: Immunity 13:715-725, 2000
NPL 12: J. Immunol. 166:7563-7570, 2001
NPL 13: J Biol. Chem. 278:1910-1914, 2003
NPL 14: Nature 421:744-748, 2003
NPL 15: J Exp Med. 198:1951-1957, 2003
NPL 16: J Clin Invest. 116:1310-1316, 2006
NPL 17: Gastroenterology 135:1130-1141, 2008
NPL 18: N. Engl. J. Med. 356: 580-592, 2007
NPL 19: Nat Med, 15(6): 633-640, 2009
NPL 20: Nat. Med. 13:139-145, 2007
NPL 21: Nat. Med. 15:633-640, 2009
NPL 22: Lupus. 9: 589-593, 2000
NPL 23: J. Immunol. 162: 494-502, 1999
NPL 24: Immunity. 17: 375-387, 2002
NPL 25: Nat. Med. 9(6): 744-749, 2003
NPL 26: J. Clin. Invest. 109:883-893, 2002
NPL 27: J Allergy Clin Immunol, 124: 809-18, 2009

SUMMARY OF INVENTION

Technical Problem

Therefore the compounds with EP4 antagonistic activities which are truly effective for ameliorating immune disease or allergy are strongly desired.

An object of the present invention is to provide compounds for use in therapeutic treatment of the human body. In particular, an object of the present invention is to provide compounds with selective EP4 receptor antagonism which are useful for treating immune disease or allergy, or preventing or delaying the onset or the progression of immune disease or allergy.

An object of the present invention is to provide a pharmaceutical composition for the treatment of immune disease which comprises a therapeutically effective amount of a compound of formula (I), (II), (III), (IV), (Va) or (Vb), or a pharmaceutically acceptable salt thereof. An object of the present invention is to provide a method for the treatment of immune disease in an animal subject including a mammalian subject, which comprises administering to the animal subject including a mammalian subject a compound of the formula (I), (II), (III), (IV), (Va) or (Vb), or a pharmaceutically acceptable salt thereof. Further an object of the present invention is to provide a method for the treatment of immune disease or allergy in an animal subject including a mammalian subject, which comprises administering to the animal subject including a mammalian subject in need a therapeutically effective amount of a compound of the formula (I), (II), (III), (IV), (Va) or (Vb), or a pharmaceutically acceptable salt thereof.

Solution to Problem

In an attempt to resolve the problems, the present inventors surprisingly discovered that a compound of formula (I), (II), (III), (IV), (Va) or (Vb), or a pharmaceutically acceptable salt thereof guarantees beneficial effects on DSS-induced colitis model.

Specifically, the gist of the present invention is as follows:
[1] Use of a compound with EP4 antagonistic activity, or a pharmaceutically acceptable salt thereof in the manufacture of a medicament for the treatment of IL-23 mediated diseases in an animal subject including a mammalian subject;
[2] Use of a compound of the formula (I), (II), (III), (IV), (Va) or (Vb), or a pharmaceutically acceptable salt thereof in the manufacture of a medicament for the treatment of IL-23 mediated diseases in an animal subject including a mammalian subject:

[Chem. 1]

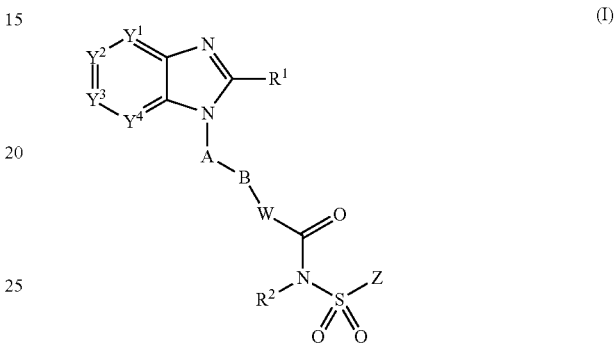

(I)

wherein $Y^1$, $Y^2$, $Y^3$, and $Y^4$ are independently selected from N, CH and C(L);

$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$ alkyl-C(=O)—N($R^3$)— or $C_{1-4}$ alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$ alkyl-O—, $Q^1$-$C_{1-4}$ alkyl-S(O)m-, $Q^1$-$C_{1-4}$ alkyl-C(O)—N($R^3$)—, $Q^1$-$C_{1-4}$ alkyl-N($R^3$)— or $C_{1-4}$ alkyl-C(O)—N($R^3$)—;

$Q^1$ is a 5-12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $R^3$N($R^4$)C(=O)—, $C_{1-4}$ alkylsulfonylamino, $C_{3-7}$ cycloalkyl, $R^3$C(=O)N($R^4$)— or $NH_2$(HN=)C—;

A is a 5-6 membered monocyclic aromatic ring optionally containing up to 3 heteroatoms selected from O, N and S, wherein said 5-6 membered monocyclic aromatic ring is optionally substituted with up to 3 substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, acetyl, $R^3$N($R^4$)C(=O)—, HO(O=)C—, $C_{1-4}$ alkyl-O(O=)C—, $C_{1-4}$ alkylsulfonylamino, $C_{3-7}$ cycloalkyl, $R^3$C(=O)N($R^4$)— and $NH_2$(HN=)C—;

B is halo-substituted $C_{1-6}$ alkylene, $C_{3-4}$ cycloalkylene, $C_{2-6}$ alkenylene, $C_{2-6}$ alkynylene, —O—$C_{1-5}$ alkylene, $C_{1-2}$ alkylene-O—C$_{1-2}$ alkylene or C$_{1-6}$ alkylene optionally substituted with an oxo group or C$_{1-3}$ alkyl;
W is NH, N—C$_{1-4}$ alkyl, O, S, N—OR$^5$ or a covalent bond;
R$^2$ is H, C$_{1-4}$ alkyl, OH or C$_{1-4}$ alkoxy;
Z is a 5-12 membered monocyclic or bicyclic aromatic ring optionally containing up to 3 heteroatoms selected from O, N and S, wherein said 5-12 membered monocyclic or bicyclic aromatic ring is optionally substituted with halo, C$_{1-4}$ alkyl, halo-substituted C$_{1-4}$ alkyl, C$_{1-4}$ alkenyl, C$_{1-4}$ alkynyl, hydroxy, C$_{1-4}$ alkoxy, halo-substituted C$_{1-4}$ alkoxy, C$_{1-4}$ alkylthio, nitro, amino, mono- or di-(C$_{1-4}$ alkyl)amino, cyano, HO—C$_{1-4}$ alkyl, C$_{1-4}$ alkoxy-C$_{1-4}$ alkyl, C$_{1-4}$ alkylsulfonyl, aminosulfonyl, C$_{1-4}$ alkylC(=O)—, R$^3$C(=O)N(R$^4$)—, HO(O=)C—, C$_{1-4}$ alkyl-O(O=)C—, C$_{1-4}$ alkylsulfonylamino, C$_{3-7}$ cycloalkyl, NH$_2$(HN=)C—, Q$^2$-S(O)m-, Q$^2$-O—, Q$^2$-N(R$^3$)— or Q$^2$-;
L is halo, C$_{1-4}$ alkyl, halo-substituted C$_{1-4}$ alkyl, hydroxy, C$_{1-4}$ alkoxy, C$_{1-4}$ alkylthio, nitro, amino, mono- or di-(C$_{1-4}$ alkyl)amino, halo-substituted C$_{1-4}$ alkoxy, cyano, HO—C$_{1-4}$ alkyl, C$_{1-4}$ alkoxy-C$_{1-4}$ alkyl, C$_{1-4}$ alkylsulfonyl, aminosulfonyl, C$_{1-4}$ alkylC(=O)—, HO(O=)C—, C$_{1-4}$ alkyl-O(O=)C—, C$_{1-4}$ alkylsulfonylamino, C$_{3-7}$ cycloalkyl, R$^3$C(=O)N(R$^4$)—, NH$_2$(HN=)C—, R$^3$N(R$^4$)C(=O)—, R$^3$N(R$^4$)S(O)m-, Q$^2$-, Q$^2$-C(=O)—, Q$^2$-O—, Q$^2$-C$_{1-4}$ alkyl-O—, or two adjacent L groups are optionally joined together to form an alkylene chain having 3 or 4 members in which one or two (non-adjacent) carbon atoms are optionally replaced by oxygen atoms;
m is 0, 1 or 2;
R$^3$ and R$^4$ are independently selected from H and C$_{1-4}$ alkyl;
R$^5$ is H, C$_{1-4}$ alkyl, C$_{1-4}$ alkyl-(O=)C— or C$_{1-4}$ alkyl-O—(O=)—C—; and
Q$^2$ is a 5-12 membered monocyclic or bicyclic aromatic ring, or a 5-12 membered tricyclic ring optionally containing up to 3 heteroatoms selected from O, N and S, wherein said 5-12 membered monocyclic or bicyclic aromatic ring is optionally substituted with halo, C$_{1-4}$ alkyl, halo-substituted C$_{1-4}$ alkyl, C$_{1-4}$ alkenyl, C$_{1-4}$ alkynyl, hydroxy, C$_{1-4}$ alkoxy, halo-substituted C$_{1-4}$ alkoxy, C$_{1-4}$ alkylthio, nitro, amino, mono- or di-(C$_{1-4}$ alkyl)amino, cyano, HO—C$_{1-4}$ alkyl, C$_{1-4}$ alkoxy-C$_{1-4}$ alkyl, C$_{1-4}$ alkylsulfonyl, aminosulfonyl, C$_{1-4}$ alkyl-(O=)C—, R$^3$(R$^4$)C(=O)N—, HO(O=)C—, C$_{1-4}$ alkyl-O(O=)C—, C$_{1-4}$ alkylsulfonylamino, C$_{3-7}$ cycloalkyl, C$_{1-4}$ alkyl-C(=O)NH— or NH$_2$(HN=)C—;

[Chem. 2]

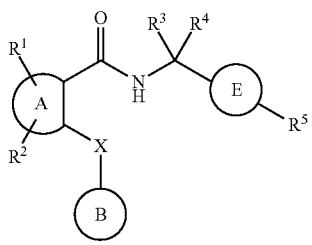

(II)

wherein A represents a phenyl group or a pyridyl group;
B represents an aryl group or a heteroaryl group;
E represents a 1,4-phenylene group;
R$^1$ and R$^2$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;
R$^3$ and R$^4$ independently represent a hydrogen atom or an alkyl group having from 1 to 4 carbon atoms; or R$^3$ and R$^4$ may be joined together to form an alkylene chain having 2 to 6 carbon atoms;
R$^5$ represents —CO$_2$H, CO$_2$W,

[Chem. 3]

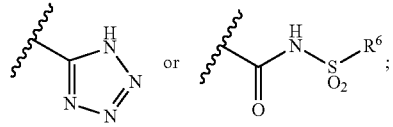

R$^6$ represents an alkyl group having from 1 to 6 carbon atoms, a cycloalkyl group having from 3 to 7 ring atoms, an aryl group or a heteroaryl group;
X represents a methylene group, an oxygen atom or a sulfur atom;
said aryl groups have from 6 to 10 carbon atoms;
said heteroaryl groups are 5 to 10-membered aromatic heterocyclic groups containing from 1 to 3 heteroatoms selected from the group consisting of sulfur atom, oxygen atom and nitrogen atom;
said aryl groups and said heteroaryl groups referred to in the definitions of B are unsubstituted or are substituted by at least one substituent selected from the group consisting of substituents alpha;
said 1,4-phenylene group referred to in the definition of E is unsubstituted or is substituted by at least one substituent selected from the group consisting of substituents beta;
said aryl groups and said heteroaryl groups referred to in the definitions of R$^6$ and alpha are unsubstituted or are substituted by at least one substituent selected from the group consisting of substituents beta;
said substituents alpha are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent alpha groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl (alkyl)amino groups having from 1 to 6 carbon atoms, alkanoylaminoalkyl groups having from 1 to 6 carbon atoms in both the alkanoyl and alkyl part, alkanoyl (alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or dialkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms; said substituents beta are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups;

W is a pharmaceutically acceptable ester prodrug group; with the proviso $R^1$ and $R^2$ do not represent a hydrogen atom simultaneously;

[Chem. 4]

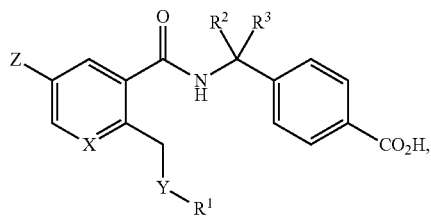

(III)

wherein X represents —CH— or a nitrogen atom;
Y represents —NR$^4$, an oxygen atom or a sulfur atom;
$R^4$ represents a hydrogen atom or an alkyl group having from 1 to 3 carbon atoms;
Z represents a hydrogen atom or a halogen atom;
$R^1$ represents an alkyl group having from 1 to 6 carbon atoms optionally substituted with an alkoxy group having from 1 to 6 carbon atoms or a cycloalkyl group having from 3 to 7 carbon atoms; a cycloalkyl group having from 3 to 7 carbon atoms optionally substituted with an alkyl group having from 1 to 3 carbon atoms; a phenyl group optionally substituted with one or more substituents alpha; or a group Het$^1$ optionally substituted with one or more substituents alpha;
Het$^1$ represents a heterocyclic group having from 4 to 7 ring atoms which contains either from 1 to 4 nitrogen ring heteroatoms or from 0 to 2 nitrogen ring heteroatoms and 1 oxygen or 1 sulfur ring heteroatom;
$R^2$ and $R^3$ independently represent a hydrogen atom or an alkyl group having from 1 to 3 carbon atoms; or $R^2$ and $R^3$ together form an alkylene chain having from 3 to 6 carbon atoms; and
said substituent alpha is selected from the group consisting of halogen atoms, alkyl groups having from 1 to 4 carbon atoms, haloalkyl groups having from 1 to 4 carbon atoms, hydroxy groups, alkoxy groups having from 1 to 4 carbon atoms, haloalkoxy groups having from 1 to 4 carbon atoms, cyano groups, hydroxy alkyl groups having from 1 to 4 carbon atoms, alkoxyalkyl groups having from 1 to 4 carbon atoms in alkoxy and alky groups, alkylsulfonyl groups having from 1 to 4 carbon atoms, alkanoyl groups having from 2 to 5 carbon atoms, alkenyl groups having from 2 to 4 carbon atoms, alkynyl groups having from 2 to 4 carbon atoms, alkylthio groups having from 1 to 4 carbon atoms, nitro groups, amino groups, mono- or di-alkylamino groups having from 1 to 4 carbon atoms, aminosulfonyl groups, alkoxycarbonyl groups having from 1 to 4 carbon atoms, alkylsulfonylamino groups having from 1 to 4 carbon atoms, cycloalkyl groups having from 3 to 7 carbon atoms and a mono- or di-alkylaminocarbonyl groups having from 1 to 6 carbon atoms;

or a pharmaceutically acceptable ester of such compound;

[Chem. 5]

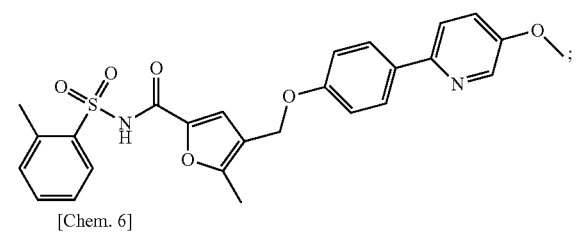

(IV)

[Chem. 6]

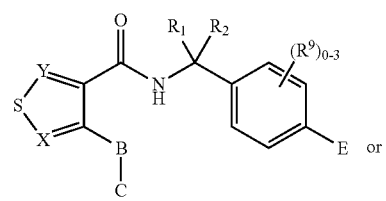

(Va)

[Chem. 7]

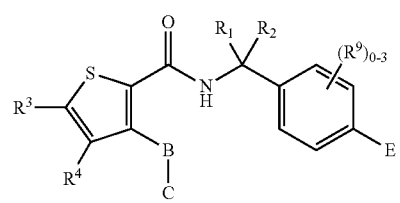

(Vb)

wherein X and Y are independently selected from the group consisting of: N and C(R$^{11}$), wherein each R$^{11}$ is independently selected from the group consisting of: hydrogen, halo and C$_{1-4}$alkyl;
B is selected from the group consisting of: —C(R$^5$)(R$^6$)—, —O—, —S—, —S(O)—, —SO$_2$—, —C(R$^5$)(R$^6$)—C(R$^7$)(R$^8$)—, —O—C(R$^5$)(R$^6$)—, —S—C(R$^5$)(R$^6$)—, —S(O)—C(R$^5$)(R$^6$)— and —SO$_2$—C(R$^5$)(R$^6$)—;
C is selected from the group consisting of aryl and heteroaryl, or a fused analog of aryl or heteroaryl, each optionally substituted with one to three substituents independently selected from R$^{10}$;
E is selected from the group consisting of: —C(O)OH, —C(O)OC$_{1-4}$alkyl, tetrazolyl and

[Chem. 8]

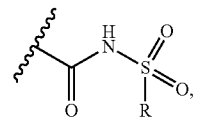

wherein R is selected from the group consisting of: C$_{1-4}$alkyl, aryl and heteroaryl, or a fused analog of aryl or heteroaryl, wherein aryl and heteroaryl or the fused analogs thereof are optionally substituted with one to three substituents independently selected from R¹⁰;

R¹ to R⁸ are independently selected from the group consisting of: H, halo, —O—R¹², $C_{1-6}$ alkyl and $C_{3-6}$cycloalkyl, and one or more pairs of R¹ and R², R⁵ and R⁶, and R⁷ and R⁸ may be joined together with the carbon atom to which they are attached to form a 3- to 5-membered monocyclic cycloalkyl ring, and R⁵ and R⁶ or R⁷ and R⁸ may be joined together to form carbonyl;

R⁹ is selected from the group consisting of: halo, hydroxyl and $C_{1-4}$alkyl;

R¹⁰ is selected from the group consisting of: halo, cyano, $C_{1-4}$alkyl, $C_{1-4}$-fluoroalkyl, $C_{1-4}$ alkoxy, $C_{1-4}$thioalkoxy and $C_{1-4}$-fluoroalkoxy; and each R¹² is selected from the group consisting of: H, $C_{1-4}$alkyl, $C_{3-6}$cycloalkyl and heterocyclyl;

[3] Use of a compound of the formula (I), (II), (III), (IV), (Va) or (Vb) in [2], or a pharmaceutically acceptable salt thereof in the manufacture of a medicament for the treatment of immune disease or allergy in an animal subject including a mammalian subject;

[4] Use of a compound of the formula (I), (II), (III), (IV), (Va) or (Vb) in [2], or a pharmaceutically acceptable salt thereof in the manufacture of a medicament for the treatment of autoimmune disease or type IV allergy in an animal subject including a mammalian subject;

[5] The use of any one of [2] to [4], wherein the compound of (I), (II), (III), or (IV) is selected from:

3-[2-(4-{2-ethyl-5,7-dimethyl-3H-imidazo[4,5-b]pyridin-3-yl}phenyl)ethyl]-1-[(4-methylbenzene)sulfonyl]urea;

3-[2-(4-{2-ethyl-4,6-dimethyl-1H-imidazo[4,5-c]pyridin-1-yl}phenyl)ethyl]-1-[(4-methylbenzene)sulfonyl]urea;

1-{2-[4-(5-acetyl-2-ethyl-1H-1,3-benzodiazol-1-yl)phenyl]ethyl}-3-[(4-methylbenzene) sulfonyl]urea;

3-{2-[4-(2-ethyl-5-methoxy-1H-1,3-benzodiazol-1-yl)phenyl]ethyl}-1-[(4-methylbenzene)sulfonyl]urea;

2-{4-[6-chloro-2-ethyl-5-(trifluoromethyl)-1H-1,3-benzodiazol-1-yl]phenyl}ethyl N-[(4-methylbenzene)sulfonyl]carbamate;

3-{2-[4-(6-chloro-5-cyano-2-ethyl-1H-1,3-benzodiazol-1-yl)phenyl]ethyl}-1-[(4-methylbenzene)sulfonyl]urea;

2-(4-{2-ethyl-4,6-dimethyl-1H-imidazo[4,5-c]pyridin-1-yl}phenyl)ethyl N-[(4-methylbenzene)sulfonyl]carbamate;

2-(4-{2-tert-butyl-4,6-dimethyl-1H-imidazo[4,5-c]pyridin-1-yl}phenyl)ethyl N-[(4-methylbenzene)sulfonyl]carbamate;

2-[4-(5-carbamoyl-6-chloro-2-ethyl-1H-1,3-benzodiazol-1-yl)phenyl]ethyl N-[(4-methylbenzene)sulfonyl]carbamate;

1-(2-{4-[2-ethyl-5-(1-hydroxyethyl)-1H-1,3-benzodiazol-1-yl]phenyl}ethyl)-3-[(4-methylbenzene)sulfonyl]urea;

1-(2-{4-[6-chloro-2-(2-hydroxypropan-2-yl)-5-(trifluoromethyl)-1H-1,3-benzodiazol-1-yl]phenyl}ethyl)-3-[(4-methylbenzene)sulfonyl]urea;

2-{4-[6-chloro-2-(pyridin-2-yl)-5-(trifluoromethyl)-1H-1,3-benzodiazol-1-yl]phenyl}ethyl N-[(4-methylbenzene)sulfonyl]carbamate;

3-(2-{5-[6-chloro-2-ethyl-5-(trifluoromethyl)-1H-1,3-benzodiazol-1-yl]pyridin-2-yl}ethyl)-1-[(4-methylbenzene)sulfonyl]urea;

2-{4-[6-chloro-2-ethyl-5-(trifluoromethyl)-1H-1,3-benzodiazol-1-yl]phenyl}ethyl N-[(2-chlorobenzene)sulfonyl]carbamate;

3-(2-{4-[5,7-dimethyl-2-(methylamino)-3H-imidazo[4,5-b]pyridin-3-yl]phenyl}ethyl)-1-[(4-methylbenzene)sulfonyl]urea;

4-((1S)-1-{[5-chloro-2-(4-fluorophenoxy)benzoyl]amino}ethyl)benzoic acid;

4-[(1S)-1-({[5-chloro-2-(4-fluorophenoxy)pyridin-3-yl]carbonyl}amino)ethyl]benzoic acid;

4-[(1S)-1-({[5-chloro-2-(3-cyanophenoxy)pyridin-3-yl]carbonyl}amino)ethyl]benzoic acid;

4-[(1S)-1-({[5-chloro-2-(3-fluorophenoxy)pyridin-3-yl]carbonyl}amino)ethyl]benzoic acid;

4-[(1S)-1-({[5-chloro-2-(3-chlorophenoxy)pyridin-3-yl]carbonyl}amino)ethyl]benzoic acid;

4-((1S)-1-{[5-chloro-2-(3-fluorophenoxy)benzoyl]amino}ethyl)benzoic acid;

4-((1S)-1-{[5-chloro-2-(3-chlorophenoxy)benzoyl]amino}ethyl)benzoic acid;

4-[(1S)-1-({[5-chloro-2-(2-chloro-4-fluorophenoxy)pyridin-3-yl]carbonyl}amino)ethyl]benzoic acid;

4-[(1S)-1-({[5-chloro-2-(3,4-difluorophenoxy)pyridin-3-yl]carbonyl}amino)ethyl]benzoic acid;

4-[(1S)-1-({[5-chloro-2-(2,3-difluorophenoxy)pyridin-3-yl]carbonyl}amino)ethyl]benzoic acid;

4-((1S)-1-{[5-chloro-2-(2,3-difluorophenoxy)benzoyl]amino}ethyl)benzoic acid;

4-((1S)-1-{[5-chloro-2-(3,4-difluorophenoxy)benzoyl]amino}ethyl)benzoic acid;

4-[(1S)-1-({[5-chloro-2-(3-chloro-5-fluorophenoxy)pyridin-3-yl]carbonyl}amino)ethyl]benzoic acid;

4-[(1S)-1-({5-chloro-2-[(4-chlorophenoxy)methyl]benzoyl}amino)ethyl]benzoic acid;

4-[(1S)-1-({5-chloro-2-[(3-chlorophenoxy)methyl]benzoyl}amino)ethyl]benzoic acid;

4-[(1S)-1-({5-chloro-2-[(4-fluorophenoxy)methyl]benzoyl}amino)ethyl]benzoic acid;

4-[(1S)-1-({5-chloro-2-[(3,4-difluorophenoxy)methyl]benzoyl}amino)ethyl]benzoic acid;

4-[(1S)-1-({5-chloro-2-[(2,4-difluorophenoxy)methyl]benzoyl}amino)ethyl]benzoic acid;

4-{(1S)-1-[({5-chloro-2-[(3-chlorophenoxy)methyl]pyridin-3-yl}carbonyl)amino]ethyl}benzoic acid;

4-[(1S)-1-({5-chloro-2-[(3,5-difluorophenoxy)methyl]benzoyl}amino)ethyl]benzoic acid;

4-[(1S)-1-({5-chloro-2-[(3-fluorophenoxy)methyl]benzoyl}amino)ethyl]benzoic acid;

4-{(1S)-1-[({2-[(4-chlorophenoxy)methyl]-5-fluoropyridin-3-yl}carbonyl)amino]ethyl}benzoic acid;

4-{(1S)-1-({5-chloro-2-[(cyclohexylmethoxy)methyl]benzoyl}amino)ethyl}benzoic acid;

4-((4-(5-methoxypyridin-2-yl)phenoxy)methyl)-5-methyl-N-(o-tolylsulfonyl)furan-2-carboxamide, 5-chloro-3-[(3-chlorophenyl)methyl]-N-[1-[4-(2H-tetrazol-5-yl)phenyl]ethyl]-2-thiophenecarboxamide, 2,5-dimethyl-N-[(1S)-1-[4-[[(methylsulfonyl)amino]carbonyl]phenyl]ethyl]-4-[[4-(trifluoromethyl)phenyl]methyl]-3-thiophenecarboxamide, 2,5-dimethyl-N-[(1S)-1-[4-[[(phenylsulfonyl)amino]carbonyl]phenyl]ethyl]-4-[[4-(trifluoromethyl)phenyl]methyl]-3-thiophenecarboxamide, 2,5-dimethyl-N-[1-[4-(2H-tetrazol-5-yl)phenyl]cyclopropyl]-4-[[3-(trifluoromethyl)phenyl]methyl]-3-thiophenecarboxamide, 2,5-dimethyl-N-[1-[4-(2H-tetrazol-5-yl)phenyl]cyclopropyl]-4-[[4-(trifluoromethyl)phenyl]methyl]-3-thiophenecarboxamide, 2-chloro-4-[[[[4-[(3-chlorophenyl)methyl]-2,5-dimethyl-3-thienyl]carbonyl]amino]methyl]-benzoic acid, 4-[(1R)-1-[[[2,5-dichloro-4-[(3-chlorophenyl)methyl]-3-thienyl]carbonyl]amino]ethyl]-benzoic acid, 4-[(1S)-1-[[[2,5-dibromo-4-[(3-chlorophenyl)methyl]-3-thienyl]carbonyl]amino]ethyl]-benzoic acid,
4-[(1S)-1-[[[2,5-dichloro-4-(3-chlorobenzoyl)-3-thienyl]carbonyl]amino]ethyl]-benzoic acid,
4-[(1S)-1-[[[2,5-dichloro-4-[(3-chlorophenyl) [(tetrahydro-2H-pyran-2-yl)oxy]methyl]-3-thienyl]carbonyl]amino]ethyl]-benzoic acid,
4-[(1S)-1-[[[2,5-dichloro-4-[(3-chlorophenyl)hydroxymethyl]-3-thienyl]carbonyl]amino]ethyl]-benzoic acid,
4-[(1S)-1-[[[2,5-dichloro-4-[(3-chlorophenyl)methyl]-3-thienyl]carbonyl]amino]ethyl]-benzoic acid,
Methyl 4-[(1S)-1-[[[2,5-dichloro-4-[(3-chlorophenyl)methyl]-3-thienyl]carbonyl]amino]ethyl]-benzoic acid,
4-[(1S)-1-[[[2,5-dichloro-4-[[3-(trifluoromethyl)phenyl]methyl]-3-thienyl]carbonyl]amino]ethyl]-benzoic acid,
4-[(1S)-1-[[[2,5-dimethyl-4-[[3-(trifluoromethyl)phenyl]methyl]-3-thienyl]carbonyl]amino]ethyl]-benzoic acid,
4-[(1S)-1-[[[2,5-dimethyl-4-[[4-(trifluoromethyl)phenyl]methyl]-3-thienyl]carbonyl]amino]ethyl]-benzoic acid,
Methyl 4-[(1S)-1-[[[2,5-dimethyl-4-[[4-(trifluoromethyl)phenyl]methyl]-3-thienyl]carbonyl]amino]ethyl]-benzoic acid,
4-[(1S)-1-[[[2,5-dimethyl-4-[[4-(trifluoromethyl)phenyl]methyl]-3-thienyl]carbonyl]amino]ethyl]-benzoic acid,
4-[(1S)-1-[[[4-[(3-chlorophenyl)methyl]-2,5-dimethyl-3-thienyl]carbonyl]amino]ethyl]-benzoic acid,
4-[(1S)-1-[[[4-[(3-chlorophenyl)methyl]-3-thienyl]carbonyl]amino]ethyl]-benzoic acid,
4-[(1S)-1-[[[4-[(4-chlorophenyl)methyl]-2,5-dimethyl-3-thienyl]carbonyl]amino]ethyl]-benzoic acid,
4-[(1S)-1-[[[5-bromo-4-[(3-chlorophenyl)methyl]-3-thienyl]carbonyl]amino]ethyl]-benzoic acid,
4-[[[[2,5-dichloro-4-[(3-chlorophenyl)methyl]-3-thienyl]carbonyl]amino]methyl]-benzoic acid,
4-[1-[[[2,5-dimethyl-4-[[3-(trifluoromethyl)phenyl]methyl]-3-thienyl]carbonyl]amino]cyclopropyl]-benzoic acid,
4-[1-[[[5-chloro-3-[(3-chlorophenyl)methyl]-2-thienyl]carbonyl]amino]ethyl]-benzoic acid, and
4-{1-[({2,5-dimethyl-4-[4-(trifluoromethyl)benzyl]-3-thienyl}carbonyl)amino]cyclopropyl}benzoic acid,
or a pharmaceutically acceptable salt thereof;
[6] The use of [5], wherein the compound of (I), (II), (III), or (IV) is selected from:
3-[2-(4-{2-ethyl-4,6-dimethyl-1H-imidazo[4,5-c]pyridin-1-yl}phenyl)ethyl]-1-[(4-methylbenzene)sulfonyl]urea;
4-[(1S)-1-({[5-chloro-2-(3-fluorophenoxy)pyridin-3-yl]carbonyl}amino)ethyl]benzoic acid;
4-{(1S)-1-[({5-chloro-2-[(3-chlorophenoxy)methyl]pyridin-3-yl}carbonyl)amino]ethyl}benzoic acid; and
4-((4-(5-methoxypyridin-2-yl)phenoxy)methyl)-5-methyl-N-(o-tolylsulfonyl)furan-2-carboxamide.
or a pharmaceutically acceptable salt thereof;
[7] The use of any one of [2] to [6], wherein the compound of the formula (I), (II), (III), (IV), (Va) or (Vb), or the pharmaceutically acceptable salt is used in combination with one or more additional compounds known to be useful in the treatment or prevention of immune disease, allergy or the symptoms thereof;
[8] A pharmaceutical composition for the treatment of IL-23 mediated diseases which comprises a therapeutically effective amount of a compound of the formula (I), (II), (III), (IV), (Va) or (Vb) in [2] or a pharmaceutically acceptable salt thereof.
[9] The pharmaceutical composition of [8], which further comprises a therapeutically effective amount of one or more additional compounds known to be useful in the treatment or prevention of immune disease, allergy or the symptoms thereof;
[10] A method for the treatment of IL-23 mediated diseases in an animal subject including a mammalian subject, which comprises administering to the animal subject including a mammalian subject a compound of the formula (I), (II), (III), (IV), (Va) or (Vb) in [2] or a pharmaceutically acceptable salt thereof;
[11] The method of [10], which further comprises administering a therapeutically effective amount of one or more additional compounds known to be useful in the treatment or prevention of immune disease or allergy thereof;
[12] A method for the treatment of IL-23 mediated diseases, which comprises administering to an animal subject including a mammalian subject in need a therapeutically effective amount of a compound of the formula (I), (II), (III), (IV), (Va) or (Vb) in [2] or a pharmaceutically acceptable salt thereof;
[13] The method of [12], which further comprises administering a therapeutically effective amount of one or more additional compounds known to be useful in the treatment or prevention of immune disease or allergy thereof; and
[14] A compound of the formula (I), (II), (III), (IV), (Va) or (Vb) in [2] or a pharmaceutically acceptable salt thereof for use in the treatment of IL-23 mediated diseases in an animal subject including a mammalian subject.

Advantageous Effects of Invention

Namely, the present inventors have discovered that a compound of formula (I), (II), (III), (IV), (Va) or (Vb), or a pharmaceutically acceptable salt thereof showed: 1) dose-dependent inhibition of IL-23 production in mouse CD11c (+) cells, 2) dose-dependent inhibition of colitis score and colon weight/length in DSS model, and 3) reduced ear swelling in a dose-dependent manner in contact hypersensitivity model.

These results clearly show that a compound of formula (I), (II), (III), (IV), (Va) or (Vb), or a pharmaceutically acceptable salt thereof is useful for the treatment and/or prevention of immune disease or allergy.

BRIEF DESCRIPTION OF DRAWINGS

FIG. 3 is a graph showing that Compound B reduces ear swelling in a dose-dependent manner during E (elicitation) and entire period.

DESCRIPTION OF EMBODIMENTS

Figure 1:
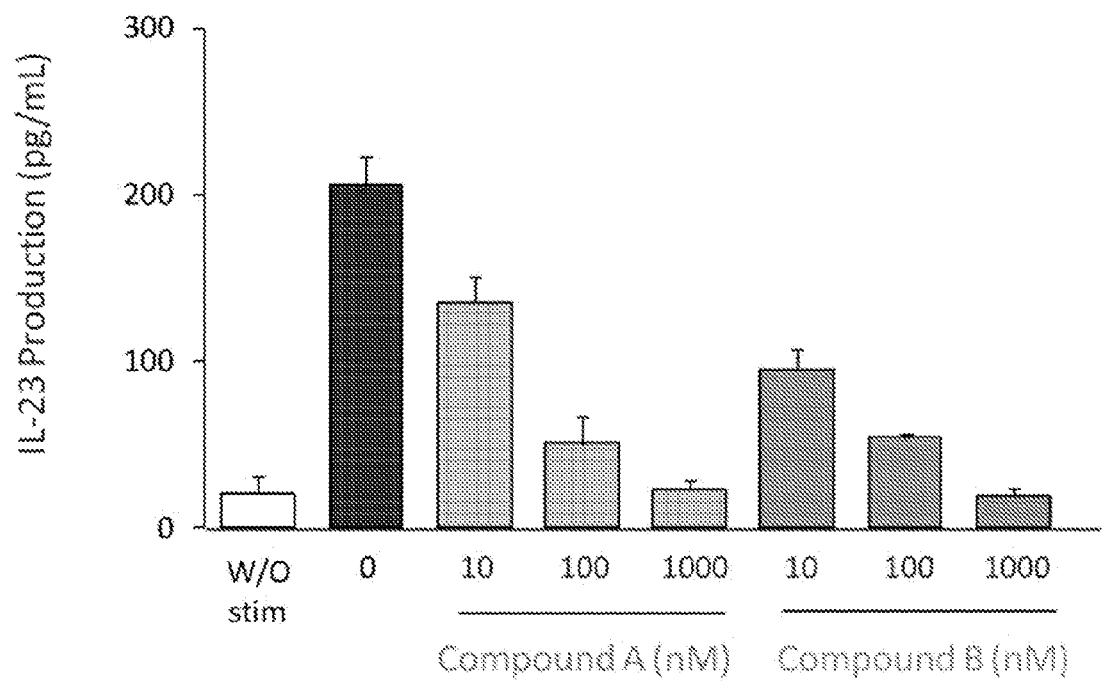
FIG. 1 is a graph showing that Compound A and Compound B inhibit IL-23 production in a dose-dependent manner in mouse CD11c (+) cells.

The present invention features the use of an EP4 receptor antagonist in the manufacture of a medicament for the treatment of IL-23 mediated diseases.

In a further aspect the invention features a method of treating IL-23 mediated diseases in an animal subject including a mammalian subject, for example, a mammal, including man, comprising administration of an effective amount of an EP4 receptor antagonist.

The term "animal subject," as used herein, includes a mammalian subject or a non-mammalian subject. Examples of suitable mammalian subject may include, without limit, human, rodents, companion animals, livestock, and primates. Suitable rodents may include, but are not limited to, mice, rats, hamsters, gerbils, and guinea pigs. Suitable companion animals may include, but are not limited to, cats, dogs, rabbits, and ferrets. Suitable livestock may include, but are not limited to, horses, goats, sheep, swine, cattle, llamas, and alpacas. Suitable primates may include, but are not limited to, chimpanzees, lemurs, macaques, marmosets, spider monkeys, squirrel monkeys, and vervet monkeys. Examples of suitable non-mammalian subject may include, without limit, birds, reptiles, amphibians, and fish. Non-limiting examples of birds include chickens, turkeys, ducks, and geese.

In a further aspect the invention features a pharmaceutical composition comprising an EP4 receptor antagonist for use in the treatment of IL-23 mediated diseases.

Preferably, the EP4 receptor antagonist used in this invention is a selective EP4 receptor antagonist.

In another preferred aspect, the EP4 receptor ligand (antagonist), which is disclosed in WO 02/32900, is an aryl or heteroaryl fused imidazole compound of the following Formula (I)

[Chem. 9]

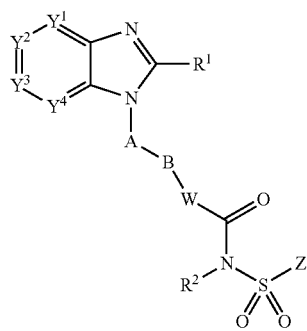

(I)

or a pharmaceutically acceptable salt thereof,
wherein
$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$ alkyl-C(=O)—N($R^3$)— or $C_{1-4}$ alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$ alkyl-O—, $Q^1$-$C_{1-4}$ alkyl-S(O)m-, $Q^1$-$C_{1-4}$ alkyl-C(O)—N($R^3$)—, $Q^1$-$C_{1-4}$ alkyl-N($R^3$)— or $C_{1-4}$ alkyl-C(O)—N($R^3$)—;

$Q^1$ is a 5-12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $R^3N(R^4)C(=O)$—, $C_{1-4}$ alkylsulfonylamino, $C_{3-7}$ cycloalkyl, $R^3C(=O)N(R^4)$— or $NH_2(HN=)C$—;

A is a 5-6 membered monocyclic aromatic ring optionally containing up to 3 heteroatoms selected from O, N and S, wherein said 5-6 membered monocyclic aromatic ring is optionally substituted with up to 3 substituents selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, acetyl, $R^3N(R^4)C(=O)$—, HO(O=)C—, $C_{1-4}$ alkyl-O(O=)C—, $C_{1-4}$ alkylsulfonylamino, $C_{3-7}$ cycloalkyl, $R^3C(=O)N(R^4)$— and $NH_2(HN=)C$—;

B is halo-substituted $C_{1-6}$ alkylene, $C_{3-7}$ cycloalkylene, $C_{2-6}$ alkenylene, $C_{2-6}$ alkynylene, —O—$C_{1-5}$ alkylene, $C_{1-2}$ alkylene-O—$C_{1-2}$ alkylene or $C_{1-6}$ alkylene optionally substituted with an oxo group or $C_{1-3}$ alkyl;

W is NH, N—$C_{1-4}$ alkyl, O, S, N—$OR^5$ or a covalent bond;

$R^2$ is H, $C_{1-4}$ alkyl, OH or $C_{1-4}$ alkoxy;

Z is a 5-12 membered monocyclic or bicyclic aromatic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, $R^3C(=O)N(R^4)$—, HO(O=)C—, $C_{1-4}$ alkyl-O(O=)C—, $C_{1-4}$ alkylsulfonylamino, $C_{3-7}$ cycloalkyl, $NH_2(HN=)C$—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, $C_{1-4}$ alkylthio, nitro, amino, mono- or di-($C_{1-4}$ alkyl)amino, halo-substituted $C_{1-4}$ alkoxy, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3C(=O)N(R^4)$—, $NH_2(HN=)C$—, $R^3N(R^4)C(=O)$—, $R^3N(R^4)S(O)m$-, $Q^2$-, $Q^2$-C(=O)—, $Q^2$-O—, $Q^2$-$C_{1-4}$ alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

$R^3$ and $R^4$ are independently selected from H and $C_{1-4}$ alkyl;

$R^5$ is H, $C_{1-4}$ alkyl, $C_{1-4}$ alkyl-(O=)C— or $C_{1-4}$ alkyl-O—(O=)—C—; and $Q^2$ is a 5-12 membered monocyclic or bicyclic aromatic ring, or a 5-12 membered tricyclic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3(R^4)C(=O)N$—, HO(O=)C—, $C_{1-4}$ alkyl-O(O=)C—, $C_{1-4}$ alkylsulfonylamino, $C_{3-7}$ cycloalkyl, $C_{1-4}$ alkyl-C(=O)NH— or $NH_2(HN=)C$—.

In the compounds of formula (I),
$Y^1$, $Y^2$, $Y^3$, and $Y^4$ are preferably independently selected from N, CH and C(L);
L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3C(=O)N(R^4)$—, $R^3N(R^4)C(=O)$—, $R^3N(R^4)S(O)m$-, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

$R^3$ and $R^4$ are independently selected from H and $C_{1-4}$ alkyl; and $Q^2$ is a 5-12 membered monocyclic or bicyclic aromatic ring, or a 8-12 membered tricyclic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3(R^4)C(=O)N$—, HO(O=)C—, $C_{1-4}$ alkyl-O(O=)C—, $C_{1-4}$ alkylsulfonylamino, $C_{3-7}$ cycloalkyl or $C_{1-4}$ alkyl-C(=O)NH—.

More preferably $Y^1$, $Y^2$, $Y^3$, and $Y^4$ are independently selected from N, CH and C(L);

L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3C(=O)N(R^4)$—, $R^3N(R^4)C(=O)$—, $R^3N(R^4)S(O)m$-, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

$R^3$ and $R^4$ are independently selected from H and $C_{1-4}$ alkyl; and $Q^2$ is a 5 or 6 membered monocyclic aromatic ring, or a 8-12 membered tricyclic ring containing up to 3 heteroatoms selected from N and S, wherein said 5 or 6 membered monocyclic aromatic ring is optionally substituted with halo, more preferably $Y^1$, $Y^2$, $Y^3$, and $Y^4$ are independently selected from N, CH and C(L);

m is 0, 1 or 2;

$R^3$ and $R^4$ are independently selected from H and $C_{1-4}$ alkyl; and $Q^2$ is a 5 or 6 membered monocyclic aromatic ring or a 8-12 membered tricyclic ring optionally containing 1 sulfur atom wherein said 5 or 6 membered monocyclic aromatic ring is optionally substituted with halo, more preferably $Y^1$, $Y^2$, $Y^3$, and $Y^4$ are independently selected from N, CH and C(L);

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, acetyl, $R^3N(R^4)C(=O)$—, $R^3N(R^4)S(O)m$-, $Q^2$-, $Q^2$-C(=O)—, $Q^2$-O—, $Q^2$-$C_{1-4}$alkyl-O—, or two adjacent L groups are joined together to form a methylenedioxy group;

$R^3$ and $R^4$ are independently selected from H and $C_{1-4}$ alkyl; and $Q^2$ is a 5 or 6 membered monocyclic aromatic ring system, more preferably $Y^1$, $Y^2$, $Y^3$, and $Y^4$ are independently selected from N, CH and C(L);

L is chloro, methyl, trifluoromethyl, hydroxy, methoxy, cyano, acetyl, —C(=O)NH$_2$, trifluoromethyloxy, methanesulfonyl, or 1-hydroxy-1-methyl-ethyl, or two adjacent L groups are joined together to form a methylenedioxy group, more preferably $Y^1$, $Y^2$, $Y^3$ and $Y^4$ are selected from the group consisting of a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
e) $Y^1$ is C(L) and $Y^2$, $Y^3$ and $Y^4$ are CH;
f) $Y^1$, $Y^3$ and $Y^4$ are CH, and $Y^2$ is C(L);
g) $Y^1$, $Y^2$ and $Y^3$ are CH, and $Y^4$ is C(L);
h) $Y^1$ and $Y^2$ are C(L), and $Y^3$ and $Y^4$ are CH;
i) $Y^1$ and $Y^3$ are C(L), and $Y^2$ and $Y^4$ are CH;
j) $Y^1$ and $Y^4$ are CH, and $Y^2$ and $Y^3$ are C(L);
k) $Y^1$ and $Y^2$ are CH, $Y^3$ is C(L) and $Y^4$ is N;
l) $Y^1$ and $Y^3$ are CH, $Y^2$ is C(L) and $Y^4$ is N;
m) $Y^1$, $Y^2$, $Y^3$ and $Y^4$ are CH;
n) $Y^1$ and $Y^2$ are C(L), $Y^3$ is CH and $Y^4$ is N;
o) $Y^1$, $Y^2$ and $Y^4$ are CH, and $Y^3$ is C(L);
p) $Y^1$ and $Y^2$ are C(L), $Y^3$ is N and $Y^4$ is CH;
q) $Y^1$ and $Y^3$ are C(L), and $Y^2$ and $Y^4$ are N;
r) $Y^1$ is C(L), $Y^2$ and $Y^3$ are CH, and $Y^4$ is N;
s) $Y^2$ is C(L), $Y^1$ and $Y^3$ are CH, and $Y^4$ is N; and
t) $Y^1$, $Y^2$ and $Y^3$ are C(L), and $Y^4$ is CH L is chloro, methyl, trifluoromethyl, hydroxy, methoxy, cyano, acetyl, —C(=O)NH$_2$, trifluoromethyloxy, methanesulfonyl, or 1-hydroxy-1-methyl-ethyl, or two adjacent L groups are joined together to form a methylenedioxy group, most preferably $Y^1$, $Y^2$, $Y^3$ and $Y^4$ are selected from the group consisting of a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
e) $Y^1$ is C(L) and $Y^2$, $Y^3$ and $Y^4$ are CH;
f) $Y^1$, $Y^3$ and $Y^4$ are CH, and $Y^2$ is C(L);
g) $Y^1$, $Y^2$ and $Y^3$ are CH, and $Y^4$ is C(L);
h) $Y^1$ and $Y^2$ are C(L), and $Y^3$ and $Y^4$ are CH;
i) $Y^1$ and $Y^3$ are C(L), and $Y^2$ and $Y^4$ are CH;
j) $Y^1$ and $Y^4$ are CH, and $Y^2$ and $Y^3$ are C(L); and
k) $Y^1$, $Y^2$ and $Y^3$ are C(L), and $Y^4$ is CH L is chloro, methyl, trifluoromethyl, hydroxy, methoxy, cyano, acetyl, —C(=O)NH$_2$, trifluoromethyloxy, methanesulfonyl, or 1-hydroxy-1-methyl-ethyl, or two adjacent L groups are joined together to form a methylenedioxy group.

In the compounds of Formula (I), $R^1$ is preferably H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$alkyl-C(=O)—N($R^3$)— or $C_{1-4}$alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$ alkyl-O—, $Q^1$-$C_{1-4}$ alkyl-S(O)m-, $Q^1$-$C_{1-4}$alkyl-C(O)—N($R^3$)—, $Q^1$-$C_{1-4}$ alkyl-N($R^3$)— or $C_{1-4}$alkyl-C(O)—N($R^3$)—;

$Q^1$ is a 5-12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$ alkylC(=O)—, HO(O=)C—, $C_{1-4}$ alkyl-O(O)C—, $R^3N(R^4)C(=O)$—, $C_{1-4}$ alkylsulfonylamino, $C_{3-7}$ cycloalkyl, $R^3C(=O)N(R^4)$— or $NH_2(HN=)C$—;

m is 0, 1 or 2; and $R^3$ is H or $C_{1-4}$ alkyl, more preferably $R^1$ is H, $C_{1-8}$ alkyl, $C_{2-8}$ alkenyl, $C_{2-8}$ alkynyl, $C_{3-7}$ cycloalkyl, $Q^1$-, pyrrolidinyl, piperidyl, oxopyrrolidinyl, oxopiperidyl, amino, mono- or di-($C_{1-8}$ alkyl)amino, wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(=O)—, $Q^1$-O—, $Q^1$-S— or $Q^1$-$C_{1-4}$ alkyl-O—, or $C_{1-4}$alkyl-C(O)—N($R^3$)—;

$Q^1$ is a 5-12 membered monocyclic aromatic ring optionally containing up to 4 heteroatoms selected from N and S, and is optionally substituted with halo, $C_{1-4}$ alkyl, $C_{1-4}$ alkylsulfonyl and $C_{1-4}$ alkylC(=O)—; and m is 0, 1 or 2, more preferably $R^1$ is H, $C_{1-8}$ alkyl, $C_{2-8}$ alkenyl, $C_{2-8}$ alkynyl, $C_{3-7}$ cycloalkyl, $Q^1$-, or mono- or di-($C_{1-8}$ alkyl)amino wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(=O)—, $Q^1$-O—, $Q^1$-S—, $Q^1$-$C_{1-4}$ alkyl-O—, or $C_{1-4}$alkyl-C(O)—N(H)—;

$Q^1$ is a 5 or 6 membered monocyclic aromatic ring optionally containing up to 4 heteroatoms selected from N and S; and m is 0, 1 or 2, more preferably $R^1$ is $C_{1-5}$ alkyl, $C_{3-7}$ cycloalkyl, or $Q^1$-, mono- or di-($C_{1-8}$ alkyl)amino wherein said $C_{1-5}$ alkyl is optionally substituted with $C_{1-3}$ alkyl, hydroxy, oxo, pyrrolidinyl, piperidyl, oxopyrrolidinyl, oxopiperidyl, $Q^1$-, or $C_{1-4}$ alkyl-C(O)—N(H)—; and $Q^1$ is a 5-12 membered monocyclic aromatic ring system optionally containing up to 2 heteroatoms selected from N and S, more preferably $R^1$ is $C_{1-5}$ alkyl, mono- or di-($C_{1-8}$ alkyl)amino, pyrrolidinyl, or pyridyl optionally substituted with $C_{1-3}$ alkyl, hydroxy, oxo, a 5 or 6 membered monocyclic aromatic ring, wherein said 5 or 6 membered monocyclic aromatic ring contains 1 or 2 heteroatoms selected from N and S, or $C_{1-4}$ alkyl-C(O)—N(H)—, most preferably $R^1$ is methyl, ethyl, n-propyl, isopropyl, n-butyl, isobutyl, neopentyl, thiazolylethyl, methylamino, dimethylamino, pyrrolidinyl, pyridyl, or 1-acetylamino-1-methylethyl.

In the compounds of Formula (I), $R^2$ is preferably H or $C_{1-4}$ alkyl, most preferably H.

In the compounds of Formula (I), A is preferably a 5-6 membered monocyclic aromatic ring optionally containing up to 2 heteroatoms selected from O, N, and S, wherein said 5-6 membered monocyclic aromatic ring is optionally substituted with up to 2 substituents selected from halo, $C_{1-4}$ alkyl, halo-substituted $C_{1-4}$ alkyl, hydroxy, $C_{1-4}$ alkoxy and halo-substituted $C_{1-4}$ alkoxy, more preferably 5-6 membered monocyclic aromatic ring optionally substituted with halo, $C_{1-4}$ alkyl or $C_{1-4}$ alkoxy, more preferably 5-6 membered monocyclic aromatic ring system optionally substituted with halo or $C_{1-4}$ alkyl, more preferably 5-6 membered monocyclic aromatic ring system, most preferably phenyl or pyridyl.

In the compounds of Formula (I), B is preferably $C_{3-7}$ cycloalkylene or $C_{1-6}$ alkylene optionally substituted with an oxo group or $C_{1-3}$ alkyl, more preferably $C_{1-3}$ alkylene optionally substituted with $C_{1-3}$ alkyl, more preferably $C_{1-2}$ alkylene optionally substituted with methyl, most preferably ethylene or propylene.

In the compounds of Formula (I), W is preferably NH, N—$C_{1-4}$ alkyl, O or N—OH, more preferably NH, N—$C_{1-2}$ alkyl or O, most preferably NH, N—$CH_3$ or O.

In the compounds of Formula (I), Z is preferably a 5-12 membered monocyclic or bicyclic aromatic ring optionally containing up to 3 heteroatoms selected from N, O, and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, hydroxy, $C_{1-4}$ alkoxy, nitro, amino, cyano, HO—$C_{1-4}$ alkyl, $C_{1-4}$ alkylsulfonyl, aminosulfonyl, $C_{1-4}$ alkylC(=O)—, $R^3$C(=O)N($R^4$)—, HO(O=)C—, $C_{1-4}$ alkyl-O(O=)C—, $C_{1-4}$ alkylsulfonylamino, $C_{1-4}$ alkyl-C(=O)NH—, $Q^2$-S(O)m-, $Q^2$-O—, $Q^2$-N($R^3$)— or $Q^2$-;

m is 0, 1 or 2;

$R^3$ and $R^4$ are independently selected from H and $C_{1-4}$ alkyl; and $Q^2$ is a 5-12 membered monocyclic or bicyclic aromatic ring, or a 8-12 membered tricyclic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3$($R^4$)C(=O)N—, HO(O=)C—, $C_{1-4}$ alkyl-O(O=)C—, $C_{1-4}$ alkylsulfonylamino, $C_{3-7}$ cycloalkyl or $C_{1-4}$ alkyl-C(=O)NH—, more preferably Z is a 5-12 membered monocyclic or bicyclic aromatic ring optionally containing up to 3 heteroatoms selected from N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3$C(=O)N($R^4$)—, $C_{1-4}$ alkyl-O(O=)C—, $Q^2$-S(O)m-, $Q^2$-O—, $Q^2$-N($R^3$)— or $Q^2$-;

m is 0, 1 or 2;

$R^3$ and $R^4$ are independently selected from H and $C_{1-4}$ alkyl; and $Q^2$ is a 5 or 6 membered monocyclic aromatic ring, or a 8-12 membered tricyclic ring containing up to 3 heteroatoms selected from N and S, wherein said 5 or 6 membered monocyclic aromatic ring is optionally substituted with halo, more preferably Z is a 5-12 membered monocyclic or bicyclic aromatic ring optionally containing up to 3 heteroatoms selected from N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3$C(=O)N($R^4$)—, $C_{1-4}$ alkyl-O(O=)C—, $Q^2$-S(O)m-, $Q^2$-O—, $Q^2$-N($R^3$)— or $Q^2$-;

m is 0, 1 or 2;

$R^3$ and $R^4$ are independently selected from H and $C_{1-4}$ alkyl; and $Q^2$ is a 5 or 6 membered monocyclic aromatic ring or a 8-12 membered tricyclic ring optionally containing 1 sulfur atom wherein said 5 or 6 membered monocyclic aromatic ring is optionally substituted with halo, more preferably Z is a 5-12 membered monocyclic or bicyclic aromatic ring optionally containing up to 3 heteroatoms selected from N and S, wherein said 5-12 membered monocyclic aromatic ring is optionally substituted with halo, $C_{1-4}$ alkyl, nitro, $R^3$C(=O)N($R^4$)— or $Q^2$-;

$R^3$ and $R^4$ are independently selected from H and $C_{1-4}$ alkyl; and $Q^2$ is a 5 or 6 membered monocyclic aromatic ring system, more preferably Z is a 5-10 membered monocyclic or bicyclic aromatic ring optionally containing up to 3 heteroatoms selected from N and S, wherein said 5-10 membered monocyclic aromatic ring is optionally substituted with chloro, bromo, methyl, nitro, $CH_3$C(=O)NH—, tBuC(O)NH— or phenyl, most preferably Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl.

A preferred group of compounds of Formula (I) includes compounds wherein $Y^1, Y^2, Y^3$, and $Y^4$ are independently selected from N, CH and C(L);

$R^1$ is H, $C_{1-8}$ alkyl, $C_{2-8}$ alkenyl, $C_{2-8}$ alkynyl, $C_{3-7}$ cycloalkyl, $C_{1-8}$ alkoxy, halo-substituted $C_{1-8}$ alkoxy, $C_{1-8}$ alkyl-S(O)m-, $Q^1$-, pyrrolidinyl, piperidyl, oxopyrrolidinyl, oxopiperidyl, amino, mono- or di-($C_{1-8}$ alkyl)amino, $C_{1-4}$alkyl-C(=O)—N($R^3$)— or $C_{1-4}$ alkyl-S(O)m-N($R^3$)—, wherein said $C_{1-8}$ alkyl, $C_{2-8}$ alkenyl and $C_{2-8}$ alkynyl are optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, 1,2,3,4-tetrahydronaphtyl, 1,2-dihydronaphtyl, pyrrolidinyl, piperidyl, oxopyrrolidinyl, oxopiperidyl, $Q^1$-, $Q^1$-C(=O)—, $Q^1$-O—, $Q^1$-S(O)m-, $Q^1$-$C_{1-4}$ alkyl-O—, $Q^1$-$C_{1-4}$ alkyl-S(O)m-, $Q^1$-$C_{1-4}$alkyl-C(=O)—N($R^3$)—, or $C_{1-4}$ alkyl-C(=O)—N($R^3$)—;

$Q^1$ is a 5-12 membered monocyclic or bicyclic aromatic ring optionally containing up to 4 heteroatoms selected from O, N and S, and is optionally substituted with halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, mono- or di-($C_{1-4}$ alkyl)amino, cyano, HO—$C_{1-4}$ alkyl, $C_{1-4}$ alkoxy-$C_{1-4}$alkyl, $C_{1-4}$ alkylsulfonyl, aminosulfonyl, $C_{1-4}$ alkylC(=O)—, HO(O=)C—, $C_{1-4}$ alkyl-O(O)C—, $R^3N(R^4)$C(=O)—, $C_{1-4}$ alkylsulfonylamino, $C_{3-7}$, cycloalkyl, $R^3$C(=O)N($R^4$)— or $NH_2$(HN=)C—;

A is a 5-6 membered monocyclic aromatic ring optionally containing up to 2 heteroatoms selected from O, N, and S, wherein said 5-6 membered monocyclic aromatic ring is optionally substituted with up to 2 substituents selected from halo, $C_{1-4}$ alkyl, halo-substituted $C_{1-4}$ alkyl, hydroxy, $C_{1-4}$ alkoxy and halo-substituted $C_{1-4}$ alkoxy;

B is $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is a 5-12 membered monocyclic or bicyclic aromatic ring optionally containing up to 3 heteroatoms selected from N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, hydroxy, $C_{1-4}$ alkoxy, nitro, amino, cyano, HO—$C_{1-4}$ alkyl, $C_{1-4}$ alkylsulfonyl, aminosulfonyl, $C_{1-4}$ alkylC(=O)—, $R^3$C(=O)N($R^4$)—, HO(O=)C—, $C_{1-4}$ alkyl-O(O=)C—, $C_{1-4}$ alkylsulfonylamino, $C_{1-4}$ alkyl-C(=O)NH—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, mono- or di-($C_{1-4}$ alkyl)amino, halo-substituted $C_{1-4}$ alkoxy, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3$C(=O)N($R^4$)—, $R^3N(R^4)$C(=O)—, $R^3N(R^4)$S(O)m-, $Q^2$-, $Q^2$C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

$R^3$ and $R^4$ are independently selected from H and $C_{1-4}$ alkyl; and $Q^2$ is a 5-12 membered monocyclic or bicyclic aromatic ring, or a 8-12 membered tricyclic ring optionally containing up to 3 heteroatoms selected from O, N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkynyl, hydroxy, $C_{1-4}$ alkoxy, halo-substituted $C_{1-4}$ alkoxy, $C_{1-4}$ alkylthio, mono- or di-($C_{1-4}$ alkyl)amino, cyano, HO—$C_{1-4}$ alkyl, $C_{1-4}$ alkoxy-$C_{1-4}$ alkyl, $C_{1-4}$ alkylsulfonyl, aminosulfonyl, $C_{1-4}$ alkyl-(O=)C—, $R^3(R^4)$C(=O)N—, HO(O=)C—, $C_{1-4}$ alkyl-O(O=)C—, $C_{1-4}$ alkylsulfonylamino, $C_{3-7}$ cycloalkyl or $C_{1-4}$ alkyl-C(=O)NH—.

A further preferred group of compounds of Formula (I) includes compounds wherein $Y^1, Y^2, Y^3$, and $Y^4$ are independently selected from N, CH and C(L);

$R^1$ is H, $C_{1-8}$ alkyl, $C_{2-8}$ alkenyl, $C_{2-8}$ alkynyl, $C_{3-7}$ cycloalkyl, $Q^1$-, pyrrolidinyl, piperidyl, oxopyrrolidinyl, oxopiperidyl, amino, mono- or di-($C_{1-8}$ alkyl)amino, wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(O)—, $Q^1$-O—, $Q^1$-S—, $Q^1$-$C_{1-4}$ alkyl-O—, or $C_{1-4}$ alkyl-C(O)—N($R^3$)—;

$Q^1$ is a 5-12 membered monocyclic aromatic ring optionally containing up to 4 heteroatoms selected from N and S, and is optionally substituted with halo, $C_{1-4}$ alkyl, $C_{1-4}$ alkylsulfonyl and $C_{1-4}$ alkylC(=O)—;

A is a 5-6 membered monocyclic aromatic ring optionally substituted with halo, $C_{1-4}$ alkyl or $C_{1-4}$ alkoxy;

B is $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is a 5-12 membered monocyclic or bicyclic aromatic ring optionally containing up to 3 heteroatoms selected from N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3$C(=O)N($R^4$)—, $C_{1-4}$ alkyl-O(O=)C—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, mono- or di-($C_{1-4}$ alkyl)amino, cyano, HO—$C_{1-4}$ alkyl, $C_{1-4}$ alkylsulfonyl, aminosulfonyl, $C_{1-4}$ alkylC(=O)—, HO(O=)C—, $C_{1-4}$ alkyl-O(O=)C—, $C_{1-4}$ alkylsulfonylamino, $C_{3-7}$ cycloalkyl, $R^3$C(=O)N($R^4$)—, $R^3N(R^4)$C(=O)—, $R^3N(R^4)$S(O)m-, $Q^2$-, $Q^2$C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

$R^3$ and $R^4$ are independently selected from H and $C_{1-4}$ alkyl; and $Q^2$ is a 5 or 6 membered monocyclic aromatic ring, or a 8-12 membered tricyclic ring containing up to 3 heteroatoms selected from N and S, wherein said 5 or 6 membered monocyclic aromatic ring is optionally substituted with halo.

A further preferred group of compounds of Formula (I) includes compounds wherein $Y^1, Y^2, Y^3$ and $Y^4$ are independently selected from N, CH and C(L);

$R^1$ is H, $C_{1-8}$ alkyl, $C_{2-8}$ alkenyl, $C_{2-8}$ alkynyl or $C_{3-7}$ cycloalkyl, wherein said $C_{1-8}$ alkyl is optionally substituted with halo, $C_{1-3}$ alkyl, hydroxy, oxo, $C_{1-4}$ alkoxy-, $C_{1-4}$ alkyl-S(O)m-, $C_{3-7}$ cycloalkyl-, cyano, indanyl, pyrrolidinyl, piperidyl, oxopyrrolidinyl, oxopiperidyl, $Q^1$-, $Q^1$-C(=O)—, $Q^1$-O—, $Q^1$-S—, $Q^1$-$C_{1-4}$ alkyl-O—, or $C_{1-4}$alkyl-C(O)—N($R^3$)—;

$Q^1$ is a 5 or 6 membered monocyclic aromatic ring optionally containing up to 4 heteroatoms selected from N and S;

A is a 5-6 membered monocyclic aromatic ring system optionally substituted with halo or $C_{1-4}$ alkyl;

B is or $C_{3-7}$ cycloalkylene or $C_{1-6}$ alkylene optionally substituted with an oxo group or $C_{1-3}$ alkyl;

W is NH, N—$C_{1-4}$ alkyl, O or N—OH;

$R^2$ is H or $C_{1-4}$ alkyl;

Z is a 5-12 membered monocyclic or bicyclic aromatic ring optionally containing up to 3 heteroatoms selected from N and S, wherein said 5-12 membered monocyclic or bicyclic aromatic ring is optionally substituted with halo, $C_{1-4}$ alkyl, halo-substituted $C_{1-4}$ alkyl, $C_{1-4}$ alkenyl, $C_{1-4}$ alkoxy, nitro, amino, cyano, $R^3$C(=O)N($R^4$)—, $C_{1-4}$ alkyl-O(O=)C—, $Q^2$-S(O)m-, $Q^2$-O—, $Q^2$-N($R^3$)— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, $C_{1-4}$ alkylsulfonyl, aminosulfonyl, $C_{1-4}$ alkylC(=O), HO(O=)C—, $C_{1-4}$ alkyl-O(O=)C—, $C_{1-4}$ alkylsulfonylamino, $C_{3-7}$ cycloalkyl, $R^3$C(=O)N$R^4$—, $R^3$N($R^4$)C(=O)—, $R^3$N($R^4$)S(O)m-, $Q^2$-, $Q^2$-C(=O)—, $Q^2$-O—, $Q^2$-$C_{1-4}$alkyl-O—, or two adjacent L groups are optionally joined together to form an alkylene chain having 3 or 4 members in which one or two (non-adjacent) carbon atoms are optionally replaced by oxygen atoms;

m is 0, 1 or 2;

$R^3$ and $R^4$ are independently selected from H and $C_{1-4}$ alkyl; and $Q^2$ is a 5 or 6 membered monocyclic aromatic ring or a 8-12 membered tricyclic ring optionally containing 1 sulfur atom wherein said 5 or 6 membered monocyclic aromatic ring is optionally substituted with halo.

A further preferred group of compounds of Formula (I) includes compounds wherein $Y^1$, $Y^2$, $Y^3$ and $Y^4$ are independently selected from N, CH and C(L);

$R^1$ is $C_{1-5}$ alkyl or $C_{3-7}$ cycloalkyl, wherein said $C_{1-5}$ alkyl is optionally substituted with $C_{1-3}$ alkyl, hydroxy, oxo, pyrrolidinyl, piperidyl, oxopyrrolidinyl, oxopiperidyl, $Q^1$-, or $C_{1-4}$alkyl-C(O)—N(H)—;

$Q^1$ is a 5-12 membered monocyclic aromatic ring system optionally containing up to 2 heteroatoms selected from N and S, A is a 5-6 membered monocyclic aromatic ring system;

B is $C_{1-3}$ alkylene optionally substituted with $C_{1-3}$ alkyl;

W is NH, N—$C_{1-2}$ alkyl or O;

$R^2$ is H;

Z is a 5-12 membered monocyclic or bicyclic aromatic ring optionally containing up to 3 heteroatoms selected from N and S, wherein said 5-12 membered monocyclic aromatic ring is optionally substituted with halo, $C_{1-4}$ alkyl, nitro, $R^3$C(=O)N($R^4$)— or $Q^2$-;

L is halo, $C_{1-4}$ alkyl, halo-substituted $C_{1-4}$ alkyl, hydroxy, $C_{1-4}$ alkoxy, halo-substituted $C_{1-4}$ alkoxy, cyano, HO—$C_{1-4}$ alkyl, acetyl, $R^3$N($R^4$)C(=O)—, $R^3$N($R^4$)S(O)m-, $Q^2$-, $Q^2$-C(=O)—, or two adjacent L groups are joined together to form a methylenedioxy group;

$R^3$ and $R^4$ are independently selected from H and $C_{1-4}$ alkyl; and $Q^2$ is a 5 or 6 membered monocyclic aromatic ring system.

A further preferred group of compounds of Formula (I) includes compounds wherein $Y^1$, $Y^2$, $Y^3$ and $Y^4$ are independently selected from N, CH and C(L);

$R^1$ is $C_{1-5}$ alkyl optionally substituted with $C_{1-3}$ alkyl, hydroxy, oxo, 5 or 6 membered monocyclic aromatic ring, wherein said 5 or 6 membered monocyclic aromatic ring is containing 1 or 2 heteroatoms selected from N and S, or $C_{1-4}$alkyl-C(O)—N($R^3$)—;

A is phenyl;

B is $C_{1-2}$ alkylene optionally substituted with methyl;

W is NH, N—$CH_3$ or O;

$R^2$ is H;

Z is a 5-10 membered monocyclic or bicyclic aromatic ring optionally containing up to 3 heteroatoms selected from N and S, wherein said 5-10 membered monocyclic aromatic ring is optionally substituted with chloro, bromo, methyl, nitro, $CH_3$C(=O)NH—, tBuC(=O)NH— or phenyl; and L is chloro, methyl, trifluoromethyl, hydroxy, methoxy, cyano, acetyl, —C(=O)$NH_2$, trifluoromethyloxy, methanesulfonyl, or 1-hydroxy-1-methyl-ethyl, or two adjacent L groups are joined together to form a methylenedioxy group.

A further preferred group of compounds of Formula (I) includes compounds wherein $Y^1$, $Y^2$, $Y^3$ and $Y^4$ are independently selected from N, CH and C(L);

$R^1$ is methyl, ethyl, n-propyl, isopropyl, n-butyl, isobutyl, neopentyl, thiazolylethyl, methylamino, dimethylamino, pyrrolidinyl, pyridyl, or 1-acetylamino-1-methylethyl;

A is phenyl;

B is ethylene or propylene;

W is NH, N—$CH_3$ or O;

$R^2$ is H;

Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and L is chloro, methyl, trifluoromethyl, hydroxy, methoxy, cyano, acetyl, —C(=O)$NH_2$, trifluoromethyloxy, methanesulfonyl, or 1-hydroxy-1-methyl-ethyl, or two adjacent L groups are joined together to form a methylenedioxy group.

A further preferred group of compounds of Formula (I) includes compounds wherein $Y^1$, $Y^2$, $Y^3$ and $Y^4$ are selected from the group consisting of a) $Y^1$ and $Y^3$ are C(L), $Y^2$ is CH and $Y^4$ is N;
b) $Y^1$ is CH, $Y^2$ and $Y^3$ are C(L) and $Y^4$ is N;
c) $Y^1$, $Y^2$ and $Y^3$ are C(L) and $Y^4$ is N;
d) $Y^1$ and $Y^3$ are C(L), $Y^2$ is N and $Y^4$ is CH;
e) $Y^1$ is C(L) and $Y^2$, $Y^3$ and $Y^4$ are CH;
f) $Y^1$, $Y^3$ and $Y^4$ are CH, and $Y^2$ is C(L);
g) $Y^1$, $Y^2$ and $Y^3$ are CH, and $Y^4$ is C(L);
h) $Y^1$ and $Y^2$ are C(L), and $Y^3$ and $Y^4$ are CH;
i) $Y^1$ and $Y^3$ are C(L), and $Y^2$ and $Y^4$ are CH;
j) $Y^1$ and $Y^4$ are CH, and $Y^2$ and $Y^3$ are C(L);
k) $Y^1$ and $Y^2$ are CH, $Y^3$ is C(L) and $Y^4$ is N;
l) $Y^1$ and $Y^3$ are CH, $Y^2$ is C(L) and $Y^4$ is N;
m) $Y^1$, $Y^2$, $Y^3$ and $Y^4$ are CH;
n) $Y^1$ and $Y^2$ are C(L), $Y^3$ is CH and $Y^4$ is N;
o) $Y^1$, $Y^2$ and $Y^4$ are CH, and $Y^3$ is C(L);
p) $Y^1$ and $Y^2$ are C(L), $Y^3$ is N and $Y^4$ is CH;
q) $Y^1$ and $Y^3$ are C(L), and $Y^2$ and $Y^4$ are N;
r) $Y^1$ is C(L), $Y^2$ and $Y^3$ are CH, and $Y^4$ is N; and
s) $Y^2$ is C(L), $Y^1$ and $Y^3$ are CH, and $Y^4$ is N;

$R^1$ is methyl, ethyl, n-propyl, isopropyl, n-butyl, isobutyl, neopentyl, thiazolylethyl, methylamino, dimethylamino, pyrrolidinyl, pyridyl, or 1-acetylamino-1-methylethyl;

A is phenyl;

B is ethylene or propylene;

W is NH, N—CH₃ or O;

R² is H;

Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and L is chloro, methyl, trifluoromethyl, hydroxy, methoxy, cyano, acetyl, —C(=O)NH₂, trifluoromethyloxy, methanesulfonyl, or 1-hydroxy-1-methyl-ethyl, or two adjacent L groups are joined together to form a methylenedioxy group.

A further preferred group of compounds of Formula (I) includes compounds wherein Y¹, Y², Y³ and Y⁴ are selected from the group consisting of a) Y¹ and Y³ are C(L), Y² is CH and Y⁴ is N;
b) Y¹ is CH, Y² and Y³ are C(L) and Y⁴ is N;
c) Y¹, Y² and Y³ are C(L) and Y⁴ is N;
d) Y¹ and Y³ are C(L), Y² is N and Y⁴ is CH;
e) Y¹ is C(L) and Y², Y³ and Y⁴ are CH;
f) Y¹, Y³ and Y⁴ are CH, and Y² is C(L);
g) Y¹, Y² and Y³ are CH, and Y⁴ is C(L);
h) Y¹ and Y² are C(L), and Y³ and Y⁴ are CH;
i) Y¹ and Y³ are C(L), and Y² and Y⁴ are CH; and
j) Y¹ and Y⁴ are CH, and Y² and Y³ are C(L);

R¹ is methyl, ethyl, n-propyl, isopropyl, n-butyl, isobutyl, neopentyl, thiazolylethyl, methylamino, dimethylamino, pyrrolidinyl, pyridyl, or 1-acetylamino-1-methylethyl;

A is phenyl;

B is ethylene or propylene;

W is NH, N—CH₃ or O;

R² is H;

Z is phenyl, pyrazolyl, thiazolyl, thiadiazolyl, thienyl, naphthyl or benzothienyl, said phenyl, pyrazolyl, thiazolyl, thiadiazolyl and thienyl being optionally substituted with one to three substituents independently selected from chloro, bromo, methyl, acetylamino, pivaloylamino, nitro and phenyl; and L is chloro, methyl, trifluoromethyl, hydroxy, methoxy, cyano, acetyl, —C(=O)NH₂, trifluoromethyloxy, methanesulfonyl, or 1-hydroxy-1-methyl-ethyl, or two adjacent L groups are joined together to form a methylenedioxy group.

Preferred individual compounds of Formula (I) are as follows:

3-(4-{2-[({[(5-chloro-1,3-dimethyl-1H-pyrazol-4-yl)sulfonyl]amino}carbonyl)amino]ethyl}phenyl)-2-ethyl-5,7-dimethyl-3H-imidazo[4,5-b]pyridine;

3-(4-{2[({[(2,4-dimethyl-1,3-thiazol-5-yl)sulfonyl]amino}carbonyl)amino]ethyl}phenyl)-2-ethyl-5,7-dimethyl-3H-imidazo[4,5-b]pyridine;

N-[5-({[({2-[4-(2-ethyl-5,7-dimethyl-3H-imidazo[4,5-b]pyridin-3-yl)phenyl]ethyl}amino)carbonyl]amino}sulfonyl)-1,3,4-thiadiazol-2-yl]acetamide;

6-ethyl-5-(4-{2-[({[(4-methylphenyl)sulfonyl]amino}carbonyl)amino]ethyl}phenyl)-5H-[1,3]dioxolo[4,5-f]benzimidazole;

6-chloro-5-cyano-2-ethyl-1-(4-{2-[({[(4-methylphenylsulfonyl]amino}carbonyl)amino]ethyl}phenyl)-1H-benzimidazole;

2-ethyl-5,7-dimethyl-3-(4-{2-[methyl({[(4-methylphenyl)sulfonyl]amino}carbonyl)amino]ethyl}phenyl)-3H-imidazo[4,5-b]pyridine;

2-ethyl-5,7-dimethyl-3-(4-{2-[({[(4-methylphenyl)sulfonyl]amino}carbonyl)amino]propyl}phenyl)-3H-imidazo[4,5-b]pyridine;

2-[4-(2-ethyl-5,7-dimethyl-3H-imidazo[4,5-b]pyridin-3-yl)phenyl]-1-methylethyl (4-methylphenyl)sulfonylcarbamate;

5,7-dimethyl-3-(4-{2-[({[(4-methylphenyl)sulfonyl]amino}carbonyl)amino]ethyl}phenyl)-2-propyl-3H-imidazo[4,5-b]pyridine;

2-isopropyl-5,7-dimethyl-3-(4-{2-[({[(4-methylphenyl)sulfonyl]amino}carbonyl)amino]ethyl}phenyl)-3H-imidazo[4,5-b]pyridine;

2-butyl-5,7-dimethyl-3-(4-{2-[({[(4-methylphenyl)sulfonyl]amino}carbonyl)amino]ethyl}phenyl)-3H-imidazo[4,5-b]pyridine;

2-isobutyl-5,7-dimethyl-3-(4-{2-[({[(4-methylphenyl)sulfonyl]amino}carbonyl)amino]ethyl}phenyl)-3H-imidazo[4,5-b]pyridine;

5,7-dimethyl-3-(4-{2-[({[(4-methylphenyl)sulfonyl]amino}carbonyl)amino]ethyl}phenyl)-2-neopentyl-3H-imidazo[4,5-b]pyridine;

5,7-dimethyl-3-(4-{2-[({[(4-methylphenyl)sulfonyl]amino}carbonyl)amino]ethyl}phenyl)-2-[2-(1,3-thiazol-2-yl)ethyl]-3H-imidazo[4,5-b]pyridine;

3-{4-[2-({[(4-biphenylsulfonyl)amino]carbonyl}amino)ethyl]phenyl}-2-ethyl-5,7-dimethyl-3H-imidazo[4,5-b]pyridine;

2-ethyl-5,7-dimethyl-3-{4-[2-({[(1-naphthylsulfonyl)amino]carbonyl}amino)ethyl]phenyl}-3H-imidazo[4,5-b]pyridine;

2-ethyl-5,7-dimethyl-3-{4-[2-({[(2-naphthylsulfonyl)amino]carbonyl}amino)ethyl]phenyl}-3H-imidazo[4,5-b]pyridine;

2-ethyl-5,7-dimethyl-3-(4-{2-[({[(2-thienyl)sulfonyl]amino}carbonyl)amino]ethyl}phenyl)-3H-imidazo[4,5-b]pyridine;

3-(4-{2-[({[(5-chloro-2-thienyl)sulfonyl]amino}carbonyl)amino]ethyl}phenyl)-2-ethyl-5,7-dimethyl-3H-imidazo[4,5-b]pyridine;

3-(4-{2-[({[(4,5-dichloro-2-thienyl)sulfonyl]amino}carbonyl)amino]ethyl}phenyl)-2-ethyl-5,7-dimethyl-3H-imidazo[4,5-b]pyridine;

3-{4-[2-({[(1-benzothien-2-ylsulfonyl)amino]carbonyl}amino)ethyl]phenyl}-2-ethyl-5,7-dimethyl-3H-imidazo[4,5-b]pyridine;

3-(4-{2-[({[(2-chlorophenyl)sulfonyl]amino}carbonyl)amino]ethyl}phenyl)-2-ethyl-5,7-dimethyl-3H-imidazo[4,5-b]pyridine;

2-ethyl-5,6-dimethyl-3-(4-{2-[({[(4-methylphenyl)sulfonyl]amino}carbonyl)amino]ethyl}phenyl)-3H-imidazo[4,5-b]pyridine;

5,6-dichloro-2-ethyl-3-(4-{2-[({[(4-methylphenyl)sulfonyl]amino}carbonyl)amino]ethyl}phenyl)-3H-imidazo[4,5-b]pyridine;

5-chloro-2-ethyl-7-methyl-3-(4-{2-[({[(4-methylphenyl)sulfonyl]amino}carbonyl)amino]ethyl}phenyl)-3H-imidazo[4,5-b]pyridine;

6-cyano-2-ethyl-5,7-dimethyl-3-(4-{2-[({[(4-methylphenyl)sulfonyl]amino}carbonyl)amino]ethyl}phenyl)-3H-imidazo[4,5-b]pyridine;

2-ethyl-4,6-dimethyl-1-(4-{2-[({[(4-methylphenyl)sulfonyl]amino}carbonyl)amino]ethyl}phenyl)-1H-imidazo[4,5-c]pyridine;

4-methyl-2-ethyl-3-(4-{2-[({[(4-methylphenyl)sulfonyl]amino}carbonyl)amino]ethyl}phenyl)benzimidazole;

7-chloro-2-ethyl-3-(4-{2-[({[(4-methylphenyl)sulfonyl]amino}carbonyl)amino]ethyl}phenyl)benzimidazole;

5-methoxy-2-ethyl-3-(4-{2-[({[(4-methylphenyl)sulfonyl]amino}carbonyl)amino]ethyl}phenyl)benzimidazole;

5-acetyl-2-ethyl-3-(4-{2-[({[(4-methylphenyl)sulfonyl]amino}carbonyl)amino]ethyl}phenyl)benzimidazole;
5-cyano-2-ethyl-1-(4-{2-[({[(4-methylphenyl)sulfonyl]amino}carbonyl)amino]ethyl}phenyl)-1H-benzimidazole;
2-ethyl-5-hydroxy-1-(4-{2-[({[(4-methylphenyl)sulfonyl]amino}carbonyl)amino]ethyl}phenyl)-1H-benzimidazole;
2-ethyl-4,5-dimethyl-1-(4-{2-[({[(4-methylphenyl)sulfonyl]amino}carbonyl)amino]ethyl}phenyl)-1H-benzimidazole;
4,6-dimethyl-2-ethyl-3-(4-{2-[({[(4-methylphenyl)sulfonyl]amino}carbonyl)amino]ethyl}phenyl)benzimidazole;
5,6-dimethyl-1-(4-{2-[({[(4-methylphenyl)sulfonyl]amino}carbonyl)amino]ethyl}phenyl)-1H-benzimidazole;
5,6-dichloro-2-ethyl-1-(4-{2-[({[(4-methylphenyl)sulfonyl]amino}carbonyl)amino]ethyl}phenyl)-1H-benzimidazole;
2-[4-(5,6-dichloro-2-ethyl-1H-benzimidazol-1-yl)phenyl]ethyl-(4-methylphenyl)sulfonylcarbamate;
6-chloro-5-trifluoromethyl-1-(4-{2-[({[(4-methylphenyl)sulfonyl]amino}carbonyl)amino]ethyl}phenyl)-1H-benzimidazole;
4-(6-chloro-2-ethyl-5-trifluoromethyl-1H-benzimidazol-1-yl)phenethyl-(4-methylphenyl)sulfonylcarbamate;
5-chloro-6-methyl-1-(4-{2-[({[(4-methylphenyl)sulfonyl]amino}carbonyl)amino]ethyl}phenyl)-1H-benzimidazole;
6-chloro-2-ethyl-1-(4-{2-[({[(4-methylphenyl)sulfonyl]amino}carbonyl)amino]ethyl}phenyl)-1H-benzimidazole-5-carboxamide;
2-ethyl-3-{4-[2-({[({3-[hydroxy(oxido)amino]phenyl}sulfonyl)amino]carbonyl}amino) ethyl]phenyl}-5,7-dimethyl-3H-imidazo[4,5-b]pyridine;
3-(4-{2-[({[(4-chlorophenyl)sulfonyl]amino}carbonyl)amino]ethyl}phenyl)-2-ethyl-5,7-dimethyl-3H-imidazo[4,5-b]pyridine;
n-[4-({[({2-[4-(2-ethyl-5,7-dimethyl-3H-imidazo[4,5-b]pyridin-3-yl)phenyl]ethyl}amino)carbonyl]amino}sulfonyl)phenyl]-2,2-dimethylpropanamide;
3-(4-{2-[({[(2-chlorophenyl)sulfonyl]amino}carbonyl)amino]ethyl}phenyl)-2-ethyl-5,7-dimethyl-3H-imidazo[4,5-b]pyridine;
3-(4-{2-[({[(3-chlorophenyl)sulfonyl]amino}carbonyl)amino]ethyl}phenyl)-2-ethyl-5,7-dimethyl-3H-imidazo[4,5-b]pyridine;
3-(4-{2-[({[(5-chloro-2-thienyl)sulfonyl]amino}carbonyl)amino]ethyl}phenyl)-2-ethyl-5,7-dimethyl-3H-imidazo[4,5-b]pyridine;
3-(4-{2-[({[(5-bromo-2-thienyl)sulfonyl]amino}carbonyl)amino]ethyl}phenyl)-2-ethyl-5,7-dimethyl-3H-imidazo[4,5-b]pyridine;
3-(4-{2-[({[(2-bromophenyl)sulfonyl]amino}carbonyl)amino]ethyl}phenyl)-2-ethyl-5,7-dimethyl-3H-imidazo[4,5-b]pyridine;
3-{4-[2-({[({4-chloro-3-nitrophenyl}sulfonyl)amino]carbonyl}amino)ethyl]phenyl}-2-ethyl-5,7-dimethyl-3H-imidazo[4,5-b]pyridine;
2-[4-(2-ethyl-4,6-dimethyl-1H-imidazo[4,5-c]pyridin-1-yl)phenyl]ethyl (4-methylphenyl)sulfonylcarbamate;
2-{4-[5,7-dimethyl-2-(methylamino)-3H-imidazo[4,5-b]pyridin-3-yl]phenyl}ethyl (4-methylphenyl)sulfonylcarbamate;
N-{[(2-{4-[5,7-dimethyl-2-(methylamino)-3H-imidazo[4,5-b]pyridin-3-yl]phenyl}ethyl)amino]carbonyl}-4-methylbenzenesulfonamide;
N-{[(2-{4-[2-ethyl-5-(1-hydroxy-1-methylethyl)-1H-benzimidazol-1-yl]phenyl}ethyl)amino]carbonyl}-4-methylbenzenesulfonamide;
2-ethyl-4,6-dimethyl-1-(4-{2-[({[(4-methylphenyl)sulfonyl]amino}carbonyl)amino]ethyl}phenyl)-1H-benzimidazole-5-carboxamide;
2-{4-[6-chloro-2-ethyl-5-(trifluoromethyl)-1H-benzimidazol-1-yl]phenyl}ethyl (2-chlorophenyl)sulfonylcarbamate;
2-{5-[6-chloro-2-ethyl-5-(trifluoromethyl)-1H-benzimidazol-1-yl]-2-pyridinyl}ethyl (4-methylphenyl)sulfonylcarbamate;
2-{4-[6-chloro-2-ethyl-5-(trifluoromethyl)-1H-benzimidazol-1-yl]phenyl}ethyl (5-methyl-2-pyridinyl)sulfonylcarbamate;
2-{4-[6-chloro-2-(1H-pyrazol-3-yl)-5-(trifluoromethyl)-1H-benzimidazol-1-yl]phenyl}ethyl(4-methylphenyl)sulfonylcarbamate;
2-{4-[6-chloro-2-(4-pyridinyl)-5-(trifluoromethyl)-1H-benzimidazol-1-yl]phenyl}ethyl (4-methylphenyl)sulfonylcarbamate;
2-{4-[5-(aminocarbonyl)-6-chloro-2-ethyl-1H-benzimidazol-1-yl]phenyl}ethyl (4-methylphenyl)sulfonylcarbamate;
N-{[(2-{4-[6-chloro-2-ethyl-5-(methylsulfonyl)-1H-benzimidazol-1-yl]phenyl}ethyl)amino]carbonyl}-4-methylbenzenesulfonamide;
2-{4-[6-chloro-2-ethyl-5-(methylsulfonyl)-1H-benzimidazol-1-yl]phenyl}ethyl (4-methylphenyl)sulfonylcarbamate;
N-[({2-[4-(2-ethyl-5,7-dimethyl-3H-imidazo[4,5-b]pyridin-3-yl)phenyl]ethyl}amino)carbonyl]-2-thiophenesulfonamide;
2-[4-(4,6-dimethyl-2-phenyl-1H-imidazo[4,5-c]pyridin-1-yl)phenyl]ethyl (4-methylphenyl)sulfonylcarbamate;
2-[4-(2-butyl-4,6-dimethyl-1H-imidazo[4,5-c]pyridin-1-yl)phenyl]ethyl (4-methylphenyl)sulfonylcarbamate;
2-{4-[6-chloro-2-ethyl-5-(trifluoromethyl)-1H-benzimidazol-1-yl]phenyl}ethyl (5-chloro-1,3-dimethyl-1H-pyrazol-4-yl)sulfonylcarbamate;
2-{4-[4,6-dimethyl-2-(3-phenylpropyl)-1H-imidazo[4,5-c]pyridin-1-yl]phenyl}ethyl (4-methylphenyl)sulfonylcarbamate;
2-{4-[6-chloro-2-(2-pyridinyl)-5-(trifluoromethyl)-1H-benzimidazol-1-yl]phenyl}ethyl (4-methylphenyl)sulfonylcarbamate;
(1S)-2-{4-[6-chloro-2-ethyl-5-(trifluoromethyl)-1H-benzimidazol-1-yl]phenyl}-1-methylethyl(4-methylphenyl)sulfonylcarbamate;
2-{6-[6-chloro-2-ethyl-5-(trifluoromethyl)-1H-benzimidazol-1-yl]-3-pyridinyl}ethyl (4-methylphenyl)sulfonylcarbamate;
N-{[(2-{4-[6-chloro-2-(1-hydroxy-1-methylethyl)-5-(trifluoromethyl)-1H-benzimidazol-1-yl]phenyl}ethyl)amino]carbonyl}-4-methylbenzenesulfonamide; and
N-{[(2-{4-[5,7-dimethyl-2-(1H-pyrazol-3-yl)-3H-imidazo[4,5-b]pyridin-3-yl]phenyl}ethyl)amino]carbonyl}-4-methylbenzenesulfonamide;
2-{4-[2-(1,1-dimethylethyl)-4,6-dimethyl-1H-imidazo[4,5-c]pyridin-1-yl]phenyl}ethyl (4-methylphenyl)sulfonylcarbamate;
2-{4-[2-[1-(acetylamino)-1-methylethyl]-6-chloro-5-(trifluoromethyl)-1H-benzimidazol-1-yl]phenyl}ethyl(4-methylphenyl)sulfonylcarbamate;
6-chloro-2-ethyl-1-(4-{2-[methyl({[(4-methylphenyl)sulfonyl]amino}carbonyl)amino]ethyl}phenyl)-1H-benzimidazole-5-carboxamide; and salts thereof.

Most preferred individual compounds of Formula (I) are following:

6-ethyl-5-(4-{2-[({[(4-methylphenyl)sulfonyl]amino}carbonyl)amino]ethyl}phenyl)-5H-[1,3]dioxolo[4,5-f]benzimidazole;

6-chloro-5-cyano-2-ethyl-1-(4-{2-[({[(4-methylphenylsulfonyl]amino}carbonyl)amino]ethyl}phenyl)-1H-benzimidazole;

2-[4-(2-ethyl-5,7-dimethyl-3H-imidazo[4,5-b]pyridin-3-yl)phenyl]-1-methylethyl (4-methylphenyl)sulfonylcarbamate;

5,7-dimethyl-3-(4-{2-[({[(4-methylphenyl)sulfonyl]amino}carbonyl)amino]ethyl}phenyl)-2-[2-(1,3-thiazol-2-yl)ethyl]-3H-imidazo[4,5-b]pyridine;

2-ethyl-5,7-dimethyl-3-(4-{2-[({[(2-thienyl)sulfonyl]amino}carbonyl)amino]ethyl}phenyl)-3H-imidazo[4,5-b]pyridine;

3-(4-{2-[({[(2-chlorophenyl)sulfonyl]amino}carbonyl)amino]ethyl}phenyl)-2-ethyl-5,7-dimethyl-3H-imidazo[4,5-b]pyridine;

2-ethyl-5,6-dimethyl-3-(4-{2-[({[(4-methylphenyl)sulfonyl]amino}carbonyl)amino]ethyl}phenyl)-3H-imidazo[4,5-b]pyridine;

5,6-dichloro-2-ethyl-3-(4-{2-[({[(4-methylphenyl)sulfonyl]amino}carbonyl)amino]ethyl}phenyl)-3H-imidazo[4,5-b]pyridine;

2-ethyl-4,6-dimethyl-1-(4-{2-[({[(4-methylphenyl)sulfonyl]amino}carbonyl)amino]ethyl}phenyl)-1H-imidazo[4,5-c]pyridine;

5-methoxy-2-ethyl-3-(4-{2-[({[(4-methylphenyl)sulfonyl]amino}carbonyl)amino]ethyl}phenyl)benzimidazole;

5-acetyl-2-ethyl-3-(4-{2-[({[(4-methylphenyl)sulfonyl]amino}carbonyl)amino]ethyl}phenyl)benzimidazole;

5-cyano-2-ethyl-1-(4-{2-[({[(4-methylphenyl)sulfonyl]amino}carbonyl)amino]ethyl}phenyl)-1H-benzimidazole;

2-ethyl-5-hydroxy-1-(4-{2-[({[(4-methylphenyl)sulfonyl]amino}carbonyl)amino]ethyl}phenyl)-1H-benzimidazole;

2-ethyl-4,5-dimethyl-1-(4-{2-[({[(4-methylphenyl)sulfonyl]amino}carbonyl)amino]ethyl}phenyl)-1H-benzimidazole;

4-(6-chloro-2-ethyl-5-trifluoromethyl-1H-benzimidazol-1-yl)phenethyl-(4-methylphenyl)sulfonylcarbamate; and 6-chloro-2-ethyl-1-(4-{2-[({[(4-methylphenyl)sulfonyl]amino}carbonyl)amino]ethyl}phenyl)-1H-benzimidazole-5-carboxamide;

2-[4-(2-ethyl-4,6-dimethyl-1H-imidazo[4,5-c]pyridin-1-yl)phenyl]ethyl (4-methylphenyl)sulfonylcarbamate;

2-{4-[5,7-dimethyl-2-(methylamino)-3H-imidazo[4,5-b]pyridin-3-yl]phenyl}ethyl (4-methylphenyl)sulfonylcarbamate;

N-{[(2-{4-[5,7-dimethyl-2-(methylamino)-3H-imidazo[4,5-b]pyridin-3-yl]phenyl}ethyl)amino]carbonyl}-4-methylbenzenesulfonamide;

N-{[(2-{4-[2-ethyl-5-(1-hydroxy-1-methylethyl)-1H-benzimidazol-1-yl]phenyl}ethyl)amino]carbonyl}-4-methylbenzenesulfonamide;

2-ethyl-4,6-dimethyl-1-(4-{2-[({[(4-methylphenyl)sulfonyl]amino}carbonyl)amino]ethyl}phenyl)-1H-benzimidazole-5-carboxamide;

2-{4-[6-chloro-2-ethyl-5-(trifluoromethyl)-1H-benzimidazol-1-yl]phenyl}ethyl (2-chlorophenyl)sulfonylcarbamate;

2-{5-[6-chloro-2-ethyl-5-(trifluoromethyl)-1H-benzimidazol-1-yl]-2-pyridinyl}ethyl (4-methylphenyl)sulfonylcarbamate;

2-{4-[6-chloro-2-ethyl-5-(trifluoromethyl)-1H-benzimidazol-1-yl]phenyl}ethyl (5-methyl-2-pyridinyl)sulfonylcarbamate;

2-{4-[6-chloro-2-(1H-pyrazol-3-yl)-5-(trifluoromethyl)-1H-benzimidazol-1-yl]phenyl}ethyl(4-methylphenyl)sulfonylcarbamate;

2-{4-[6-chloro-2-(4-pyridinyl)-5-(trifluoromethyl)-1H-benzimidazol-1-yl]phenyl}ethyl (4-methylphenyl)sulfonylcarbamate;

2-{4-[5-(aminocarbonyl)-6-chloro-2-ethyl-1H-benzimidazol-1-yl]phenyl}ethyl (4-methylphenyl)sulfonylcarbamate;

N-{[(2-{4-[6-chloro-2-ethyl-5-(methylsulfonyl)-1H-benzimidazol-1-yl]phenyl}ethyl)amino]carbonyl}-4-methylbenzenesulfonamide;

2-{4-[6-chloro-2-ethyl-5-(methylsulfonyl)-1H-benzimidazol-1-yl]phenyl}ethyl (4-methylphenyl)sulfonylcarbamate;

N-[({2-[4-(2-ethyl-5,7-dimethyl-3H-imidazo[4,5-b]pyridin-3-yl)phenyl]ethyl}amino)carbonyl]-2-thiophenesulfonamide;

2-[4-(4,6-dimethyl-2-phenyl-1H-imidazo[4,5-c]pyridin-1-yl)phenyl]ethyl (4-methylphenyl)sulfonylcarbamate;

2-[4-(2-butyl-4,6-dimethyl-1H-imidazo[4,5-c]pyridin-1-yl)phenyl]ethyl (4-methylphenyl)sulfonylcarbamate;

2-{4-[6-chloro-2-ethyl-5-(trifluoromethyl)-1H-benzimidazol-1-yl]phenyl}ethyl (5-chloro-1,3-dimethyl-1H-pyrazol-4-yl)sulfonylcarbamate;

2-{4-[4,6-dimethyl-2-(3-phenylpropyl)-1H-imidazo[4,5-c]pyridin-1-yl]phenyl}ethyl (4-methylphenyl)sulfonylcarbamate;

2-{4-[6-chloro-2-(2-pyridinyl)-5-(trifluoromethyl)-1H-benzimidazol-1-yl]phenyl}ethyl (4-methylphenyl)sulfonylcarbamate;

(1S)-2-{4-[6-chloro-2-ethyl-5-(trifluoromethyl)-1H-benzimidazol-1-yl]phenyl}-1-methylethyl(4-methylphenyl)sulfonylcarbamate;

2-{6-[6-chloro-2-ethyl-5-(trifluoromethyl)-1H-benzimidazol-1-yl]-3-pyridinyl}ethyl (4-methylphenyl)sulfonylcarbamate;

N-{[(2-{4-[6-chloro-2-(1-hydroxy-1-methylethyl)-5-(trifluoromethyl)-1H-benzimidazol-1-yl]phenyl}ethyl)amino]carbonyl}-4-methylbenzenesulfonamide; and N-{[(2-{4-[5,7-dimethyl-2-(1H-pyrazol-3-yl)-3H-imidazo[4,5-b]pyridin-3-yl]phenyl}ethyl)amino]carbonyl}-4-methylbenzenesulfonamide;

2-{4-[2-(1,1-dimethylethyl)-4,6-dimethyl-1H-imidazo[4,5-c]pyridin-1-yl]phenyl}ethyl (4-methylphenyl)sulfonylcarbamate;

2-{4-[2-[1-(acetylamino)-1-methylethyl]-6-chloro-5-(trifluoromethyl)-1H-benzimidazol-1-yl]phenyl}ethyl(4-methylphenyl)sulfonylcarbamate;

6-chloro-2-ethyl-1-(4-{2-[methyl({[(4-methylphenyl)sulfonyl]amino}carbonyl)amino]ethyl}phenyl)-1H-benzimidazole-5-carboxamide; and salts thereof.

In another preferred aspect, the EP4 receptor ligand (antagonist), which is disclosed in WO 2005/021508, is phenyl or pyridyl amide compounds of the following Formula (II) or pharmaceutically acceptable salts thereof,

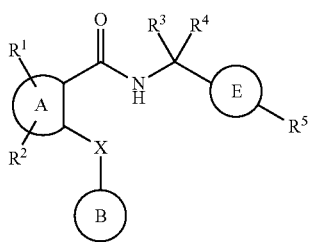

(II)

wherein A represents a phenyl group or a pyridyl group; B represents an aryl group or a heteroaryl group;

E represents a 1,4-phenylene group;

$R^1$ and $R^2$ independently represent a hydrogen atom, a halogen atom, an alkyl group having from 1 to 4 carbon atoms, an alkoxy group having from 1 to 4 carbon atoms, a haloalkyl group having from 1 to 4 carbon atoms, a haloalkoxy group having from 1 to 4 carbon atoms, a cyano group or an aminocarbonyl group;

$R^3$ and $R^4$ independently represent a hydrogen atom or an alkyl group having from 1 to 4 carbon atoms; or $R^3$ and $R^4$ may be joined together to form an alkylene chain having 2 to 6 carbon atoms;

$R^5$ represents —$CO_2H$, $CO_2W$,

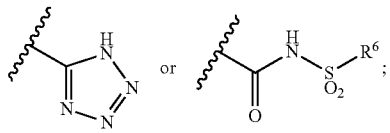

$R^6$ represents an alkyl group having from 1 to 6 carbon atoms, a cycloalkyl group having from 3 to 7 ring atoms, an aryl group or a heteroaryl group;

X represents a methylene group, an oxygen atom or a sulfur atom;

said aryl groups have from 6 to 10 carbon atoms; said heteroaryl groups are 5 to 10-membered aromatic heterocyclic groups containing from 1 to 3 heteroatoms selected from the group consisting of sulfur atom, oxygen atom and nitrogen atom;

said aryl groups and said heteroaryl groups referred to in the definitions of B are unsubstituted or are substituted by at least one substituent selected from the group consisting of substituents alpha;

said 1,4-phenylene group referred to in the definition of E is unsubstituted or is substituted by at least one substituent selected from the group consisting of substituents beta;

said aryl groups and said heteroaryl groups referred to in the definitions of $R^6$ and alpha are unsubstituted or are substituted by at least one substituent selected from the group consisting of substituents beta;

said substituents alpha are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent alpha groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl (alkyl)amino groups having from 1 to 6 carbon atoms, alkanoylaminoalkyl groups having from 1 to 6 carbon atoms in both the alkanoyl and alkyl part, alkanoyl (alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or dialkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms;

said substituents beta are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms and cyano groups;

W is a pharmaceutically acceptable ester prodrug group; with the proviso $R^1$ and $R^2$ do not represent a hydrogen atom simultaneously.

A preferred compound of formula (II) of this invention is that wherein B represents an aryl or heteroaryl group such as phenyl, naphthyl, pyridyl, quinolyl or isoquinolyl. B is preferably unsubstituted or is substituted by at least one substituent selected from the group consisting of substituents alpha; said substituents alpha are selected from the group consisting halogen atoms (e.g. fluoro, chloro), alkyl groups having from 1 to 4 carbon atoms (e.g. methyl, ethyl), alkoxy groups having from 1 to 4 carbon atoms (e.g. methoxy), haloalkoxy groups having from 1 to 4 carbon atoms (e.g. trifluoromethoxy), cyano groups, alkynyl groups having from 2 to 6 carbon atoms (e.g. ethynyl), alkanoyl groups having from 1 to 5 carbon atoms (e.g. acetyl), cycloalkyl groups having from 3 to 7 ring atoms (e.g. cyclopentyl), heteroaryl groups (e.g. 2-, 3- or 4-pyridyl, 1-methylimidazol-2-yl, thiazol-2-yl, 2-methylthiazol-4-yl), aryl groups (e.g. phenyl), aralkoxy groups having from 7 to 10 carbon atoms (e.g. benzyloxy), arylcarbonyl groups (e.g. benzoyl), two adjacent alpha groups are optionally joined together to form an alkylene chain having 3 carbon atoms, alkylthio groups having from 1 to 4 carbon atoms (e.g. methylthio) and di-alkylaminoalkyl groups having from 1 to 6 carbon atoms in the alkyl part; said heteroaryl groups referred to in the definitions of alpha are unsubstituted or are substituted by alkyl groups having from 1 to 4 carbon atoms (e.g. methyl). More preferably B represents a phenyl group optionally substituted by substituent selected from the group consisting of substituents alpha; said substituents alpha are selected from the group consisting of halogen atoms (e.g. fluoro, chloro), alkyl groups having from 1 to 4 carbon atoms (e.g. methyl, ethyl), alkoxy groups having from 1 to 4 carbon atoms (e.g. methoxy), haloalkoxy groups having from 1 to 4 carbon atoms (e.g. trifluoromethoxy), cyano groups, alkynyl groups having from 2 to 6 carbon atoms (e.g. ethynyl), alkanoyl groups having from 1 to 4 carbon atoms (e.g. acetyl), cycloalkyl groups having from 3 to 7 ring atoms (e.g. cyclopentyl), alkylthio groups having from 1 to 4 carbon atoms (e.g. methylthio), di-alkylaminoalkyl groups having from 1 to 6 carbon atoms in the alkyl part, thiazolyl groups, isothiazolyl groups, oxazolyl groups, isoxazolyl groups, imidazolyl groups, pyridyl groups, benzyloxy groups, phenyl groups or benzoyl groups; said thiazolyl groups, isothiazolyl groups, oxazolyl groups, isoxazolyl groups, imidazolyl groups and pyridyl groups referred to in the definitions of alpha are unsubstituted or are substituted by alkyl groups having from 1 to 4 carbon atoms. More preferably B represents a phenyl group optionally substituted by substituent selected from the group consisting of substituents alpha; said substituents alpha are selected from the group consisting of fluorine atoms, chlorine atoms, methyl groups, ethyl groups, methoxy groups, trifluoromethoxy groups, cyano groups, ethynyl groups, acetyl groups, cyclopentyl groups, methylthio groups, dimethylaminoethyl groups, phenyl groups, imidazolyl groups optionally substituted by methyl groups, thiazolyl groups optionally substituted by methyl groups, pyridyl groups or benzyloxy groups. More preferably, B represents a phenyl group substituted by 1 or 2 fluoro or chloro substituents. More preferably, B represents a phenyl group substituted by 1 fluoro or chloro substituent.

Most preferably, B represents 3-fluorophenyl.

A preferred compound of formula (II) of this invention is that wherein X represents a methylene group or an oxygen atom. Preferably, X represents an oxygen atom.

A preferred compound of formula (II) of this invention is that wherein $R^1$ and $R^2$ independently represent a hydrogen atom, a fluorine atom, a chlorine atom, trifluoromethyl, cyano or aminocarbonyl. A preferred compound of formula (II) of this invention is that wherein $R^1$ represents a halogen atom (e.g. fluoro, chloro) and $R^2$ represents a hydrogen atom.

A preferred compound of formula (II) of this invention is that wherein $R^3$ and $R^4$ independently represent a hydrogen atom or an alkyl group having from 1 to 4 carbon atoms (e.g. methyl, ethyl). More preferably $R^3$ represents an alkyl group having from 1 to 4 carbon atoms (e.g. methyl, ethyl) and $R^4$ represents a hydrogen atom. Most preferably $R^3$ represents a methyl group and $R^4$ represents a hydrogen atom.

A preferred compound of formula (II) of this invention is that wherein $R^5$ represents —CO$_2$H,

[Chem. 12]

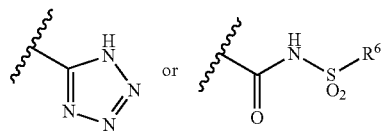

and $R^6$ represents an aryl group optionally substituted by halogen atoms or is a heteroaryl group. More preferably, $R^5$ represents —CO$_2$H,

[Chem. 13]

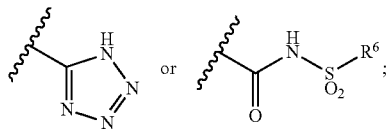

and $R^6$ represents an aryl group optionally substituted by halogen atoms. Preferably $R^6$ is methyl, cyclohexyl, 2-, 3- or 4-chlorophenyl, 3-fluorophenyl, 3-methylphenyl, 3-methoxyphenyl or 5-methyl-2-pyridyl. Further more preferably $R^5$ represents —CO$_2$H or

[Chem. 14]

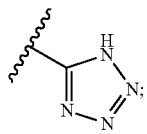

and $R^6$ represents a phenyl group optionally substituted by halogen atoms. Most preferably $R^5$ represents —CO$_2$H. In the definition of B, aryl is preferably phenyl or naphthyl and heteroaryl is a 5- to 10-membered aromatic heterocyclic group containing either from 1 to 3 nitrogen heteroatoms, or 1 or 2 nitrogen heteroatoms and/or 1 oxygen or 1 sulphur heteroatom.

Particularly preferred compounds of the invention include those in which each variable in Formula (II) is selected from the preferred groups for each variable.

Even more preferable compounds of the invention include those where each variable in Formula (II) is selected from the more preferred groups for each variable.

A preferred individual compound of Formula (II) is selected from 4-((1S)-1-{[5-chloro-2-(4-fluorophenoxy)benzoyl]amino}ethyl)benzoic acid; 4-[(1S)-1-({[5-chloro-2-(4-fluorophenoxy)pyridin-3-yl]carbonyl}amino)ethyl]benzoic acid; 4-[(1S)-1-({[5-chloro-2-(3-cyanophenoxy)pyridin-3-yl]carbonyl}amino)ethyl]benzoic acid; 4-[(1S)-1-({[5-chloro-2-(3-fluorophenoxy)pyridin-3-yl]carbonyl}amino)ethyl]benzoic acid; 4-[(1S)-1-({[5-chloro-2-(3-chlorophenoxy)pyridin-3-yl]carbonyl}amino)ethyl]benzoic acid; 4-[(1S)-1-({[5-chloro-2-(3-fluorophenoxy)benzoyl]amino}ethyl)benzoic acid; 4-[(1S)-1-({[5-chloro-2-(3-methoxyphenoxy)benzoyl]amino}ethyl)benzoic acid; 4-((1S)-1-{[5-chloro-2-(3-chlorophenoxy)benzoyl]amino}ethyl)benzoic acid; 4-[(1S)-1-({[5-chloro-2-(2,4-difluorophenoxy)pyridin-3-yl]carbonyl}amino)ethyl]benzoic acid; 4-[(1S)-1-({[5-chloro-2-(4-chloro-3-fluorophenoxy)pyridin-3-yl]carbonyl}amino)ethyl]benzoic acid; 4-[(1S)-1-({[5-chloro-2-(2-chloro-4-fluorophenoxy)pyridin-3-yl]carbonyl}amino) ethyl]benzoic acid; 4-[(1S)-1-({[5-chloro-2-(2,6-difluorophenoxy)pyridin-3-yl]carbonyl}amino)ethyl]benzoic acid; 4-[(1S)-1-({[5-chloro-2-(3,4-difluorophenoxy)pyridin-3-yl]carbonyl}amino)ethyl]benzoic acid; 4-{(1S)-1-[({5-chloro-2-[3-(1,3-thiazol-2-yl)phenoxy]pyridin-3-yl}carbonyl)amino]ethyl}benzoic acid; 4-[(1S)-1-({[5-chloro-2-(2,3-difluorophenoxy)pyridin-3-yl]carbonyl}amino)ethyl]benzoic acid; 4-[(1S)-1-({[5-chloro-2-(2,5-difluorophenoxy)pyridin-3-yl]carbonyl}amino)ethyl]benzoic acid; 4-[(1S)-1-({[5-chloro-2-(4-chlorophenoxy)pyridin3-yl]carbonyl}amino)ethyl]benzoic acid; 4-[(1S)-1-({[5-chloro-2-(4-chloro-2-fluorophenoxy)

pyridin-3-yl]carbonyl}amino)ethyl]benzoic acid; 4-[(S)-1-({[5-chloro-2-(2-chloro-5-fluorophenoxy)pyridin-3-yl]carbonyl}amino)ethyl]benzoic acid; 4-[(1S)-1-({[5-chloro-2-(3-methylphenoxy)pyridin-3-yl]carbonyl}amino) ethyl]benzoic acid; 4-[(1S)-1-({[5-chloro-2-(4-fluoro-3-methylphenoxy)pyridin-3-yl]carbonyl}amino)ethyl]benzoic acid; 4-[(1S)-1-({[5-chloro-2-(3,5-difluorophenoxy)pyridin-3-yl]carbonyl}amino)ethyl]benzoic acid; 4-((1S)-1-{[5-chloro-2-(2,3-difluorophenoxy)benzoyl]amino}ethyl)benzoic acid; 4-((1S)-1-{[5-chloro-2-(2,4-difluorophenoxy)benzoyl]amino}ethyl)benzoic acid; 4-((1S)-1-{[5-chloro-2-(3,4-difluorophenoxy)benzoyl]amino}ethyl)benzoic acid; 4-[(1S)-1-({[5-chloro-2-(3-chloro-5-fluorophenoxy)pyridin-3-yl]carbonyl}amino) ethyl]benzoic acid; 4-[(1S)-1-({[5-chloro-2-(3-chloro-2-methylphenoxy)pyridin-3-yl]carbonyl}amino)ethyl]benzoic acid; 4-((1S)-1-{[5-chloro-2-(3,5-difluorophenoxy)benzoyl]amino}ethyl)benzoic acid; 4-((1S)-1-{[5-chloro-2-(2,5-difluorophenoxy)benzoyl]amino}ethyl)benzoic acid; 4-[(1S)-1-({[5-chloro-2-(3-chloro-2-fluorophenoxy)pyridin-3-yl]carbonyl}amino) ethyl]benzoic acid; 4-[(1S)-1-({[5-chloro-2-(3-pyridin-2-ylphenoxy)pyridin-3-yl]carbonyl}amino)ethyl]benzoic acid; 4-[(1S)-1-({[5-chloro-2-(4-pyridin-2-ylphenoxy)pyridin-3-yl]carbonyl}amino)ethyl]benzoic acid; 4-[(1S)-1-({[5-chloro-2-(4-pyridin-4-ylphenoxy)pyridin-3-yl]carbonyl}amino)ethyl]benzoic acid; 4-[(1S)-1-({[5-chloro-2-(3-chloro-5-methylphenoxy)pyridin-3-yl]carbonyl}amino)ethyl]benzoic acid; 4-((1S)-1-{[5-chloro-2-(3-methylphenoxy)benzoyl]amino}ethyl)benzoic acid; 4-((1S)-1-{[5-chloro-2-(3-chloro-5-fluorophenoxy)benzoyl]amino}ethyl)benzoic acid; 4-((1S)-1-{[5-chloro-2-(2,6-difluorophenoxy)benzoyl]amino}ethyl)benzoic acid; 4-((1S)-1-{[5-chloro-2-phenoxypyridin-3-yl)carbonyl]amino}ethyl)benzoic acid; 4-[(1S)-1-({[5-chloro-2-(2,3-dimethylphenoxy)pyridin-3-yl]carbonyl}amino)ethyl]benzoic acid; 4-[(1S)-1-({[5-chloro-2-(2,3-dichlorophenoxy)pyridin-3-yl]carbonyl)amino)ethyl]benzoic acid; 4-[(1S)-1-({[5-chloro-2-(3,4-dichlorophenoxy)pyridin-3-yl]carbonyl}amino)ethyl]benzoic acid; 4-[(1S)-1-({[5-chloro-2-(3,5-dichlorophenoxy)pyridin-3-yl]carbonyl}amino)ethyl]benzoic acid; and 4[(1S)-1-({[5-chloro-2-(3-fluoro-4-methylphenoxy)pyridin-3-yl]carbonyl}amino)ethyl]benzoic acid; or a pharmaceutically acceptable salt thereof.

A further preferred individual compound of Formula (II) is selected from 4-((1S)-1-{[5-chloro-2-(4-fluorophenoxy)benzoyl]amino}ethyl)benzoic acid; 4[(1S)-1-({[5-chloro-2-(4-fluorophenoxy)pyridin-3-yl]carbonyl}amino)ethyl]benzoic acid; 4-[(1S)-1-({[5-chloro-2-(3-cyanophenoxy)pyridin-3-yl]carbonyl}amino)ethyl]benzoic acid; 4[(1S)-1-({[5-chloro-2-(3-fluorophenoxy)pyridin-3-yl]carbonyl}amino)ethyl]benzoic acid; 4-[(1S)-1-({[5-chloro-2-(3-chlorophenoxy)pyridin-3-yl]carbonyl}amino)ethyl]benzoic acid; 4-((1S)-1-{[5-chloro-2-(3-fluorophenoxy)benzoyl]amino}ethyl)benzoic acid; 4-((1S)-1-{[5-chloro-2-(3-chlorophenoxy)benzoyl]amino}ethyl)benzoic acid; 4-[(1S)-1-({[5-chloro-2-(2-chloro-4-fluorophenoxy)pyridin-3-yl]carbonyl}amino)ethyl]benzoic acid; 4-[(1S)-1-({[5-chloro-2-(2,6-difluorophenoxy)pyridin-3-yl]carbonyl}amino)ethyl]benzoic acid; 4-[(1S)-1-({[5-chloro-2-(3,4-difluorophenoxy)pyridin-3-yl]carbonyl}amino)ethyl]benzoic acid; 4-[(1S)-1-({[5-chloro-2-(2,3-difluorophenoxy)pyridin-3-yl]carbonyl}amino)ethyl]benzoic acid; 4-[(1S)-1-({[5-chloro-2-(2,5-difluorophenoxy)pyridin-3-yl]carbonyl}amino)ethyl]benzoic acid; 4-[(1S)-1-({[5-chloro-2-(2-chloro-5-fluorophenoxy)pyridin-3-yl]carbonyl}amino)ethyl]benzoic acid; 4-[(1S)-1-({[5-chloro-2-(3-methylphenoxy)pyridin-3-yl]carbonyl}amino)ethyl]benzoic acid; 4-[(1S)-1-({[5-chloro-2-(3,5-difluorophenoxy)pyridin-3-yl]carbonyl}amino)ethyl]benzoic acid; 4-((1S)-1-{[5-chloro-2-(2,3-difluorophenoxy)benzoyl]amino}ethyl)benzoic acid; 4-((1S)-1-{[5-chloro-2-(3,4-difluorophenoxy)benzoyl]amino}ethyl)benzoic acid; 4-[(1S)-1-({[5-chloro-2-(3-chloro-5-fluorophenoxy)pyridin-3-yl]carbonyl}amino) ethyl]benzoic acid; 4-((1S)-1-{[5-chloro-2-(3,5-difluorophenoxy)benzoyl]amino}ethyl)benzoic acid; 4-((1S)-1-{[5-chloro-2-(2,5-difluorophenoxy)benzoyl]amino}ethyl)benzoic acid; 4-[(1S)-1-({[5-chloro-2-(3-chloro-5-methylphenoxy)pyridin-3-yl]carbonyl}amino) ethyl]benzoic acid; 4-((1S)-1-{[5-chloro-2-(3-methylphenoxy)benzoyl]amino}ethyl)benzoic acid; 4-((1S)-1-{[5-chloro-2-(3-chloro-5-fluorophenoxy)benzoyl]amino}ethyl)benzoic acid; 4-((1S)-1-{[5-chloro-2-(2,6-difluorophenoxy)benzoyl]amino}ethyl)benzoic acid; 4-((1S)-1-{[(5-chloro-2-phenoxypyridin-3-yl)carbonyl]amino}ethyl)benzoic acid; 4-[(1S)-1-({[5-chloro-2-(2,3-dichlorophenoxy)pyridin-3-yl]carbonyl}amino) ethyl]benzoic acid; 4-[(1S)-1-({[5-chloro-2-(3,4-dichlorophenoxy)pyridin-3-yl]carbonyl}amino)ethyl]benzoic acid; 4-[(1S)-1-({[5-chloro-2-(3,5-dichlorophenoxy)pyridin-3-yl]carbonyl}amino)ethyl]benzoic acid; and 4-[(1S)-1-({[5-chloro-2-(3-fluoro-4-methylphenoxy)pyridin-3-yl]carbonyl}amino)ethyl]benzoic acid; or a pharmaceutically acceptable salt thereof.

In another preferred aspect, the EP4 receptor ligand (antagonist), which is disclosed in WO 05/105732, is substituted methyl aryl or heteroaryl amide compounds of the following Formula (III)

[Chem. 15]

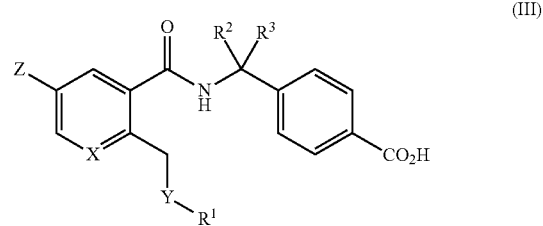

(III)

wherein X represents —CH— or a nitrogen atom;
Y represents —NR$^4$, an oxygen atom or a sulfur atom;
R$^4$ represents a hydrogen atom or an alkyl group having from 1 to 3 carbon atoms;
Z represents a hydrogen atom or a halogen atom;
R$^1$ represents an alkyl group having from 1 to 6 carbon atoms optionally substituted with an alkoxy group having from 1 to 6 carbon atoms or a cycloalkyl group having from 3 to 7 carbon atoms; a cycloalkyl group having from 3 to 7 carbon atoms optionally substituted with an alkyl group having from 1 to 3 carbon atoms; a phenyl group optionally substituted with one or more substituents alpha; or a group Het$^1$ optionally substituted with one or more substituents alpha;
Het$^1$ represents a heterocyclic group having from 4 to 7 ring atoms which contains either from 1 to 4 nitrogen ring heteroatoms or from 0 to 2 nitrogen ring heteroatoms and 1 oxygen or 1 sulfur ring heteroatom;
R$^2$ and R$^3$ independently represent a hydrogen atom or an alkyl group having from 1 to 3 carbon atoms; or R$^2$ and R$^3$ together form an alkylene chain having from 3 to 6 carbon atoms; and said substituent alpha is selected from the group consisting of halogen atoms, alkyl groups having from 1 to 4 carbon atoms, haloalkyl groups having from 1 to 4 carbon atoms, hydroxy groups, alkoxy groups having from 1 to 4 carbon atoms, haloalkoxy groups having from 1 to 4 carbon atoms, cyano groups, hydroxy alkyl groups having from 1 to 4 carbon atoms, alkoxyalkyl groups having from 1 to 4 carbon atoms in alkoxy and alky groups, alkylsulfonyl groups having from 1 to 4 carbon atoms, alkanoyl groups having from 2 to 5 carbon atoms, alkenyl groups having from 2 to 4 carbon atoms, alkynyl groups having from 2 to 4 carbon atoms, alkylthio groups having from 1 to 4 carbon atoms, nitro groups, amino groups, mono- or di-alkylamino groups having from 1 to 4 carbon atoms, aminosulfonyl groups, alkoxycarbonyl groups having from 1 to 4 carbon atoms, alkylsulfonylamino groups having from 1 to 4 carbon atoms, cycloalkyl groups having from 3 to 7 carbon atoms and a mono- or di-alkylaminocarbonyl groups having from 1 to 6 carbon atoms;

or a pharmaceutically acceptable ester of such compound; or a pharmaceutically acceptable salt thereof.

A preferred compound of formula (III) of this invention is that wherein Y represents $NR^4$ or an oxygen atom; and $R^4$ represents an alkyl group having from 1 to 3 carbon atoms. More preferably, Y represents $NCH_3$ or an oxygen atom. Most preferably, Y represents an oxygen atom A preferred compound of formula (III) of this invention is that wherein Z represents a halogen atom. More preferably, Z represents a chlorine atom or a fluorine atom.

A preferred compound of formula (III) of this invention is that wherein $R^1$ represents an alkyl group having from 1 to 6 carbon atoms; a cycloalkyl group having from 3 to 7 carbon atoms, a phenyl group optionally substituted with one or more substituents alpha; or a group $Het^1$ optionally substituted with one or more substituents alpha;

$Het^1$ represents a heterocyclic group having from 5 to 6 ring atoms which contains either from 1 to 2 nitrogen ring heteroatoms or from 0 to 2 nitrogen ring heteroatoms and 1 oxygen or 1 sulfur ring heteroatom; said substituents alpha are selected from the group consisting of halogen atoms, alkyl groups having from 1 to 4 carbon atoms, haloalkyl groups having from 1 to 4 carbon atoms, hydroxy groups, alkoxy groups having from 1 to 4 carbon atoms, haloalkoxy groups having from 1 to 4 carbon atoms, cyano groups, hydroxy alkyl groups having from 1 to 4 carbon atoms, alkoxyalkyl groups having from 1 to 4 carbon atoms in alkoxy and alky groups, alkylsulfonyl groups having from 1 to 4 carbon atoms and alkanoyl groups having from 2 to 5 carbon atoms. More preferably, $R^1$ represents an alkyl group having from 1 to 6 carbon atoms, a cycloalkyl group having from 4 to 6 carbon atoms, a phenyl group, a pyridyl group, an oxazolyl group, a pyrazolyl group, a thiazolyl group, a tetrahydrofuranyl group or a tetrahydropyranyl group; said phenyl group, pyridyl group, oxazolyl group, pyrazolyl group, thiazolyl group, tetrahydrofuranyl group and tetrahydropyranyl group referred to in the definitions of $R^1$ are unsubstituted or are substituted by at least one substituent selected from the group consisting of substituents alpha; said substituents alpha are selected from the group consisting of halogen atoms, alkyl groups having from 1 to 2 carbon atoms and cyano groups. More preferably, $R^1$ represents a butyl group, a pyridyl group, a phenyl group, an oxazolyl group, a pyrazolyl group or a thiazolyl group; said phenyl group, pyridyl group, oxazolyl group, pyrazolyl group, thiazolyl group referred to in the definitions of $R^1$ are unsubstituted or are substituted by 1 to 2 substituent selected from the group consisting of substituents alpha; said substituents alpha are selected from the group consisting of halogen atoms and alkyl groups having from 1 to 2 carbon atoms. Most preferably, $R^1$ represents a phenyl group, optionally substituted by 1 to 2 groups independently selected from a fluorine atom, a chlorine atom and a methyl group.

A preferred compound of formula (III) of this invention is that wherein $R^2$ and $R^3$ independently represent a hydrogen atom or an alkyl group having from 1 to 3 carbon atoms. More preferably, $R^2$ represents a hydrogen atom; and $R^3$ represents a methyl group.

Particularly preferred compounds of the invention include those in which each variable in Formula (III) is selected from the preferred groups for each variable. Even more preferable compounds of the invention include those where each variable in Formula (III) is selected from the more preferred groups for each variable.

A preferred individual compound of Formula (III) is selected from

4-[(1S)-1-({5-Chloro-2-[(4-chlorophenoxy)methyl]benzoyl}amino)ethyl]benzoic acid;

4-[(1S)-1-({5-Chloro-2-[(4-methylphenoxy)methyl]benzoyl}amino)ethyl]benzoic acid;

4-[(1S)-1-({5-Chloro-2-[(3-chlorophenoxy)methyl]benzoyl}amino)ethyl]benzoic acid;

4[(1S)-1-({5-Chloro-2-[(4-fluorophenoxy)methyl]benzoyl}amino)ethyl]benzoic acid;

4-[(1S)-1-({5-Chloro-2-[(2,3-difluorophenoxy)methyl]benzoyl}amino)ethyl]benzoic acid;

4-[(1S)-1-({5-Chloro-2-[(3,4-difluorophenoxy)methyl]benzoyl}amino)ethyl]benzoic acid;

4-[(1S)-1-({5-Chloro-2-[(2,4-difluorophenoxy)methyl]benzoyl}amino)ethyl]benzoic acid;

4-{(1S)-1-[({5-Chloro-2-[(3-chlorophenoxy)methyl]pyridin-3-yl}carbonyl)amino]ethyl}benzoic acid;

4-[(1S)-1-({5-Chloro-2-[(2-chlorophenoxy)methyl]benzoyl}amino)ethyl]benzoic acid;

4-[(1S)-1-({5-Chloro-2-[(3,5-difluorophenoxy)methyl]benzoyl}amino)ethyl]benzoic acid;

4-{(1S)-1-[({5-Chloro-2-[(4-chlorophenoxy)methyl]pyridin-3-yl}carbonyl)amino]ethyl}benzoic acid;

4[(1S)-1-({5-Chloro-2-[(3-fluorophenoxy)methyl]benzoyl}amino)ethyl]benzoic acid;

4-[(1S)-1-({5-Chloro-2-[(2,6-difluorophenoxy)methyl]benzoyl}amino)ethyl]benzoic acid;

4[(1S)-1-({5-Chloro-2-[(2-fluorophenoxy)methyl]benzoyl}amino)ethyl]benzoic acid;

4-[(1S)-1-({5-Chloro-2-[(2,5-difluorophenoxy)methyl]benzoyl}amino)ethyl]benzoic acid; and 4-{(1S)-1-[({2-[(4-Chlorophenoxy)methyl]-5-fluoropyridin-3-yl}carbonyl)amino]ethyl}benzoic acid;

or a pharmaceutically acceptable ester of such compound;

or a pharmaceutically acceptable salt thereof.

In another preferred aspect, the EP4 receptor ligand (antagonist), which is disclosed in WO 2004/067524, is a compound of the following Formula (IV) or a pharmaceutically acceptable salt thereof.

[Chem. 16]

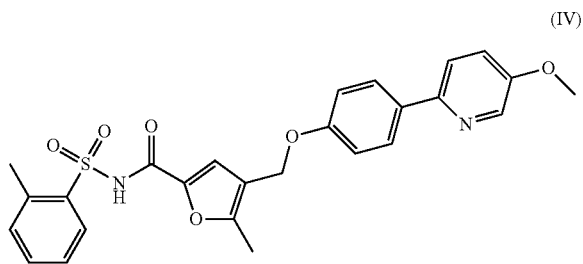

(IV)

A more preferred compound of Formula (IV) is sodium (4-((4-(5-methoxypyridin-2-yl)phenoxy)methyl)-5-methyl-furan-2-carbonyl)(o-tolylsulfonyl)amide.

In another preferred aspect, the EP4 receptor ligand (antagonist), which is disclosed in Marc Blouim et al., J. Med. Chem. (DOI 10.1021/jm901771h) and WO2008/017164, is a compound of the following Formula (Va) or (Vb), or a pharmaceutically acceptable salt thereof:

[Chem. 17]

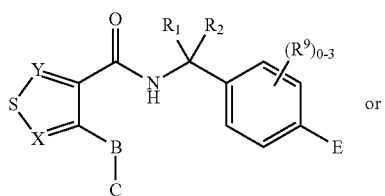

(Va)

or

[Chem. 18]

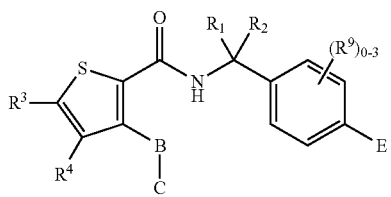

(Vb)

wherein X and Y are independently selected from the group consisting of: N and $C(R^{11})$, wherein each $R^{11}$ is independently selected from the group consisting of: hydrogen, halo and $C_{1-4}$alkyl;

B is selected from the group consisting of: —$C(R^5)(R^6)$—, —O—, —S—, —S(O)—, —SO$_2$—, —$C(R^5)(R^6)$—$C(R^7)(R^8)$—, —O—$C(R^5)(R^6)$—, —S—$C(R^5)(R^6)$—, —S(O)—$C(R^5)(R^6)$— and —SO$_2$—$C(R^5)(R^6)$—;

C is selected from the group consisting of aryl and heteroaryl, or a fused analog of aryl or heteroaryl, each optionally substituted with one to three substituents independently selected from $R^{10}$;

E is selected from the group consisting of: —C(O)OH, —C(O)O$C_{1-4}$alkyl, tetrazolyl and

[Chem. 19]

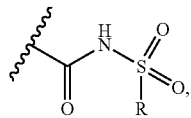

wherein R is selected from the group consisting of: $C_{1-4}$alkyl, aryl and heteroaryl, or a fused analog of aryl or heteroaryl, wherein aryl and heteroaryl or the fused analogs thereof are optionally substituted with one to three substituents independently selected from $R^{10}$;

$R^1$ to $R^8$ are independently selected from the group consisting of: H, halo, —O—$R^{12}$, $C_{1-6}$ alkyl and $C_{3-6}$cycloalkyl, and one or more pairs of $R^1$ and $R^2$, $R^5$ and $R^6$, and $R^7$ and $R^8$ may be joined together with the carbon atom to which they are attached to form a 3- to 5-membered monocyclic cycloalkyl ring, and $R^5$ and $R^6$ or $R^7$ and $R^8$ may be joined together to form carbonyl;

$R^9$ is selected from the group consisting of: halo, hydroxyl and $C_{1-4}$alkyl;

$R^{10}$ is selected from the group consisting of: halo, cyano, $C_{1-4}$alkyl, $C_{1-4}$-fluoroalkyl, $C_{1-4}$ alkoxy, $C_{1-4}$thioalkoxy and $C_{1-4}$-fluoroalkoxy; and each $R^{12}$ is selected from the group consisting of: H, $C_{1-4}$alkyl, $C_{3-6}$cycloalkyl and heterocyclyl.

A preferred individual compound of Formula (Va) or (Vb), is selected from 5-chloro-3-[(3-chlorophenyl)methyl]-N-[1-[4-(2H-tetrazol-5-yl)phenyl]ethyl]-2-thiophenecarboxamide, 2,5-dimethyl-N-[(1S)-1-[4-[[(methylsulfonyl)amino]carbonyl]phenyl]ethyl]-4-[[4-(trifluoromethyl)phenyl]methyl]-3-thiophenecarboxamide, 2,5-dimethyl-N-[(1S)-1-[4-[[(phenylsulfonyl)amino]carbonyl]phenyl]ethyl]-4-[[4-(trifluoromethyl)phenyl]methyl]-3-thiophenecarboxamide, 2,5-dimethyl-N-[1-[4-(2H-tetrazol-5-yl)phenyl]cyclopropyl]-4-[[3-(trifluoromethyl)phenyl]methyl]-3-thiophenecarboxamide, 2,5-dimethyl-N-[1-[4-(2H-tetrazol-5-yl)phenyl]cyclopropyl]-4-[[4-(trifluoromethyl)phenyl]methyl]-3-thiophenecarboxamide, 2-chloro-4-[[[[4-[(3-chlorophenyl)methyl]-2,5-dimethyl-3-thienyl]carbonyl]amino]methyl]-benzoic acid, 4-[(1R)-1-[[[2,5-dichloro-4-[(3-chlorophenyl)methyl]-3-thienyl]carbonyl]amino]ethyl]-benzoic acid, 4-[(1S)-1-[[[2,5-dibromo-4-[(3-chlorophenyl)methyl]-3-thienyl]carbonyl]amino]ethyl]-benzoic acid, 4-[(1S)-1-[[[2,5-dichloro-4-(3-chlorobenzoyl)-3-thienyl]carbonyl]amino]ethyl]-benzoic acid, 4-[(1S)-1-[[[2,5-dichloro-4-[(3-chlorophenyl) [(tetrahydro-2H-pyran-2-yl)oxy]methyl]-3-thienyl]carbonyl]amino]ethyl]-benzoic acid, 4-[(1S)-1-[[[2,5-dichloro-4-[(3-chlorophenyl)hydroxymethyl]-3-thienyl]carbonyl]amino]ethyl]-benzoic acid, 4-[(1S)-1-[[[2,5-dichloro-4-[(3-chlorophenyl)methyl]-3-thienyl]carbonyl]amino]ethyl]-benzoic acid, Methyl 4-[(1S)-1-[[[2,5-dichloro-4-[(3-chlorophenyl)methyl]-3-thienyl]carbonyl]amino]ethyl]-benzoic acid, 4-[(1S)-1-[[[2,5-dichloro-4-[[3-(trifluoromethyl)phenyl]methyl]-3-thienyl]carbonyl]amino]ethyl]-benzoic acid, 4-[(1S)-1-[[[2,5-dimethyl-4-[[3-(trifluoromethyl)phenyl]methyl]-3-thienyl]carbonyl]amino]ethyl]-benzoic acid, 4-[(1S)-1-[[[2,5-dimethyl-4-[[4-(trifluoromethyl)phenyl]methyl]-3-thienyl]carbonyl]amino]ethyl]-benzoic acid, Methyl 4-[(1S)-1-[[[2,5-dimethyl-4-[[4-(trifluoromethyl)phenyl]methyl]-3-thienyl]carbonyl]amino]ethyl]-benzoic acid, 4-[(1S)-1-[[[2,5-dimethyl-4-[[4-(trifluoromethyl)phenyl]methyl]-3-thienyl]carbonyl]amino]ethyl]-benzoic acid, 4-[(1S)-1-[[[4-[(3-chlorophenyl)methyl]-2,5-dimethyl-3-thienyl]carbonyl]amino]ethyl]-benzoic acid, 4-[(1S)-1-[[[4-[(3-chlorophenyl)methyl]-3-thienyl]carbonyl]amino]ethyl]-benzoic acid,
4-[(1S)-1-[[[4-[(4-chlorophenyl)methyl]-2,5-dimethyl-3-thienyl]carbonyl]amino]ethyl]-benzoic acid,
4-[(1S)-1-[[[5-bromo-4-[(3-chlorophenyl)methyl]-3-thienyl]carbonyl]amino]ethyl]-benzoic acid,
4-[[[[2,5-dichloro-4-[(3-chlorophenyl)methyl]-3-thienyl]carbonyl]amino]methyl]-benzoic acid,
4-[1-[[[2,5-dimethyl-4-[[3-(trifluoromethyl)phenyl]methyl]-3-thienyl]carbonyl]amino]cyclopropyl]-benzoic acid,
4-[1-[[[5-chloro-3-[(3-chlorophenyl)methyl]-2-thienyl]carbonyl]amino]ethyl]-benzoic acid, and
4-{1-[({2,5-dimethyl-4-[4-(trifluoromethyl)benzyl]-3-thienyl}carbonyl)amino]cyclopropyl}benzoic acid.

A preferred compound of this invention is selected from:
3-[2-(4-{2-ethyl-5,7-dimethyl-3H-imidazo[4,5-b]pyridin-3-yl}phenyl)ethyl]-1-[(4-methylbenzene)sulfonyl]urea;
3-[2-(4-{2-ethyl-4,6-dimethyl-1H-imidazo[4,5-c]pyridin-1-yl}phenyl)ethyl]-1-[(4-methylbenzene)sulfonyl]urea;
1-{2-[4-(5-acetyl-2-ethyl-1H-1,3-benzodiazol-1-yl)phenyl]ethyl}-3-[(4-methylbenzene)sulfonyl]urea;
3-{2-[4-(2-ethyl-5-methoxy-1H-1,3-benzodiazol-1-yl)phenyl]ethyl}-1-[(4-methylbenzene)sulfonyl]urea;
2-{4-[6-chloro-2-ethyl-5-(trifluoromethyl)-1H-1,3-benzodiazol-1-yl]phenyl}ethyl N-[(4-methylbenzene)sulfonyl]carbamate;
3-{2-[4-(6-chloro-5-cyano-2-ethyl-1H-1,3-benzodiazol-1-yl)phenyl]ethyl}-1-[(4-methylbenzene)sulfonyl]urea;
2-(4-{2-ethyl-4,6-dimethyl-1H-imidazo[4,5-c]pyridin-1-yl}phenyl)ethyl N-[(4-methylbenzene)sulfonyl]carbamate;
2-(4-{2-tert-butyl-4,6-dimethyl-1H-imidazo[4,5-c]pyridin-1-yl}phenyl)ethyl N-[(4-methylbenzene)sulfonyl]carbamate;
2-[4-(5-carbamoyl-6-chloro-2-ethyl-1H-1,3-benzodiazol-1-yl)phenyl]ethyl N-[(4-methylbenzene)sulfonyl]carbamate;
1-(2-{4-[2-ethyl-5-(1-hydroxyethyl)-1H-1,3-benzodiazol-1-yl]phenyl}ethyl)-3-[(4-m ethylbenzene)sulfonyl]urea;
1-(2-{4-[6-chloro-2-(2-hydroxypropan-2-yl)-5-(trifluoromethyl)-1H-1,3-benzodiazol-1-yl]phenyl}ethyl)-3-[(4-methylbenzene)sulfonyl]urea;
2-{4-[6-chloro-2-(pyridin-2-yl)-5-(trifluoromethyl)-1H-1,3-benzodiazol-1-yl]phenyl}ethyl N-[(4-methylbenzene)sulfonyl]carbamate;
3-(2-{5-[6-chloro-2-ethyl-5-(trifluoromethyl)-1H-1,3-benzodiazol-1-yl]pyridin-2-yl}ethyl)-1-[(4-methylbenzene)sulfonyl]urea;
2-{4-[6-chloro-2-ethyl-5-(trifluoromethyl)-1H-1,3-benzodiazol-1-yl]phenyl}ethyl N-[(2-chlorobenzene)sulfonyl]carbamate;
3-(2-{4-[5,7-dimethyl-2-(methylamino)-3H-imidazo[4,5-b]pyridin-3-yl]phenyl}ethyl)-1-[(4-methylbenzene)sulfonyl]urea;
4-((1S)-1-{[5-chloro-2-(4-fluorophenoxy)benzoyl]amino}ethyl)benzoic acid;
4-[(1S)-1-({[5-chloro-2-(4-fluorophenoxy)pyridin-3-yl]carbonyl}amino)ethyl]benzoic acid;
4-[(1S)-1-({[5-chloro-2-(3-cyanophenoxy)pyridin-3-yl]carbonyl}amino)ethyl]benzoic acid;
4-[(1S)-1-({[5-chloro-2-(3-fluorophenoxy)pyridin-3-yl]carbonyl}amino)ethyl]benzoic acid;
4-[(1S)-1-({[5-chloro-2-(3-chlorophenoxy)pyridin-3-yl]carbonyl}amino)ethyl]benzoic acid;
4-((1S)-1-{[5-chloro-2-(3-fluorophenoxy)benzoyl]amino}ethyl)benzoic acid;
4-((1S)-1-{[5-chloro-2-(3-chlorophenoxy)benzoyl]amino}ethyl)benzoic acid;
4-[(1S)-1-({[5-chloro-2-(2-chloro-4-fluorophenoxy)pyridin-3-yl]carbonyl}amino)ethyl]benzoic acid;
4-[(1S)-1-({[5-chloro-2-(3,4-difluorophenoxy)pyridin-3-yl]carbonyl}amino)ethyl]benzoic acid;
4-[(1S)-1-({[5-chloro-2-(2,3-difluorophenoxy)pyridin-3-yl]carbonyl}amino)ethyl]benzoic acid;
4-((1S)-1-{[5-chloro-2-(2,3-difluorophenoxy)benzoyl]amino}ethyl)benzoic acid;
4-((1S)-1-{[5-chloro-2-(3,4-difluorophenoxy)benzoyl]amino}ethyl)benzoic acid;
4-[(1S)-1-({[5-chloro-2-(3-chloro-5-fluorophenoxy)pyridin-3-yl]carbonyl}amino)ethyl]benzoic acid;
4-[(1S)-1-({5-chloro-2-[(4-chlorophenoxy)methyl]benzoyl}amino)ethyl]benzoic acid;
4-[(1S)-1-({5-chloro-2-[(3-chlorophenoxy)methyl]benzoyl}amino)ethyl]benzoic acid;
4-[(1S)-1-({5-chloro-2-[(4-fluorophenoxy)methyl]benzoyl}amino)ethyl]benzoic acid;
4-[(1S)-1-({5-chloro-2-[(3,4-difluorophenoxy)methyl]benzoyl}amino)ethyl]benzoic acid;
4-[(1S)-1-({5-chloro-2-[(2,4-difluorophenoxy)methyl]benzoyl}amino)ethyl]benzoic acid;
4-{(1S)-1-[({5-chloro-2-[(3-chlorophenoxy)methyl]pyridin-3-yl}carbonyl)amino]ethyl}benzoic acid;
4-[(1S)-1-({5-chloro-2-[(3,5-difluorophenoxy)methyl]benzoyl}amino)ethyl]benzoic acid;
4-[(1S)-1-({5-chloro-2-[(3-fluorophenoxy)methyl]benzoyl}amino)ethyl]benzoic acid;
4-{(1S)-1-[({2-[(4-chlorophenoxy)methyl]-5-fluoropyridin-3-yl}carbonyl)amino]ethyl}benzoic acid;
4-{(1S)-1-({5-chloro-2-[(cyclohexylmethoxy)methyl]benzoyl}amino)ethyl}benzoic acid;
4-((4-(5-methoxypyridin-2-yl)phenoxy)methyl)-5-methyl-N-(o-tolylsulfonyl)furan-2-carboxamide; and
4-{1-[({2,5-dimethyl-4-[4-(trifluoromethyl)benzyl]-3-thienyl}carbonyl)amino]cyclopropyl}benzoic acid,
or a pharmaceutically acceptable salt thereof.

Those skilled in the art will fully understand the terms used herein in the description and the appendant claims to describe the present invention. Nonetheless, unless otherwise provided herein, the following terms are as described immediately below.

By "IL-23 mediated disease" is meant the disease caused by IL-23.

Examples of such IL-23 mediated diseases include immune disease and allergy.

By "EP4 receptor antagonist" is meant a chemical substance that reduces or attenuates the biological activity of an EP4 receptor. Such antagonists may include proteins such as anti-EP4 antibodies, nucleic acids, amino acids, peptides carbohydrates, small molecules (organic or inorganic), or any other compound or composition which decreases the activity of an EP4 receptor either by reducing the amount of EP4 receptor present in a cell, or by decreasing the binding or signaling activity of the EP4 receptor.

The term "alkyl", as used herein, means a straight or branched saturated monovalent hydrocarbon radical including, but not limited to, methyl, ethyl, propyl, isopropyl, n-butyl, iso-butyl, sec-butyl, tert-butyl, neopentyl and the like.

The term "alkenyl", as used herein, means a hydrocarbon radical having at least one double bond including, but not limited to, ethenyl, propenyl, 1-butenyl, 2-butenyl and the like.

The term "alkynyl", as used herein, means a hydrocarbon radical having at least one triple bond including, but not limited to, ethynyl, propynyl, 1-butynyl, 2-butynyl and the like.

The term "halo", as used herein, refers to F, Cl, Br or I, preferably F or Cl.

The term "cycloalkyl", as used herein, means a saturated carbocyclic radical including, but not limited to, cyclopropyl, cyclobutyl, cyclohexyl, cycloheptyl, cyclooctyl, cyclononyl, cyclodecyl and the like.

The term "alkoxy", as used herein, means an O-alkyl group wherein "alkyl" is defined above.

The term "monocyclic aromatic ring", as used herein, means a monocyclic aromatic carbocyclic or heterocyclic ring (and containing 0-4 heteroatoms selected from O, N and S) including, but not limited to, phenyl, pyrazolyl, furyl, thienyl, oxazolyl, tetrazolyl, thiazolyl, imidazolyl, thiadiazolyl, pyridyl, pyrimidinyl, pyrrolyl, thiophenyl, pyrazinyl, pyridazinyl, isooxazolyl, isothiazolyl, triazolyl, furazanyl and the like.

The term "bicyclic aromatic ring", as used herein, means a monocyclic or bicyclic aromatic carbocyclic or heterocyclic ring (and containing 0-4 heteroatoms selected from O, N and S) including, but not limited to, naphthyl, benzofuranyl, isobenzofuranyl, benzothiophenyl, indolyl, isoindolyl, benzoxazolyl, benzothiazolyl, indazolyl, benzimidazolyl, quinolyl, isoquinolyl, cinnolinyl, phthalazinyl, quinazolinyl, quinoxalinyl and the like.

The term "alkylene", as used herein, means a saturated hydrocarbon (straight chain or branched) wherein a hydrogen atom is removed from each of the terminal carbons such as methylene, ethylene, propylene, butylene, pentylene, hexylene and the like.

The term "cycloalkylene", as used herein, means divalent cycloalkyl groups including, but not limited to, cyclopropylene, cyclobutylene, cyclopentylene, cyclohexylene and cycloheptylene and the like.

The term "alkenylene", as used herein, means a straight or branched hydrocarbon chain spacer radical having at least one double bond including, but not limited to, —CH=CH—, —CH=CHCH—, —CH=CHCH(CH$_3$)—, and the like.

The term "alkynylene", as used herein, means a straight or branched hydrocarbon chain spacer radical having at least one triple bond including, but not limited to,

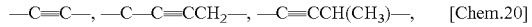
—C≡C—, —C—C≡CCH$_2$—, —C≡CCH(CH$_3$)—,  [Chem.20]

and the like.

The term "tricyclic ring", as used herein, means a saturated carbocyclic radical including, but not limited to, adamantyl, tricyclo[5.2.1.0$^{2,6}$]decane, and the like.

The term "two adjacent L groups are optionally joined together to form an alkylene chain having 3 or 4 members in which one or two (non-adjacent) carbon atoms are optionally replaced by oxygen atoms", as used herein, means, but not limited to, —O—CH$_2$—O—, —CH$_2$—O—CH$_2$—, —O—CH$_2$CH$_2$—, —CH$_2$CH$_2$—O—, —O—CH$_2$CH$_2$—O—, —CH$_2$CH$_2$CH$_2$—O—, O—CH$_2$CH$_2$CH$_2$—, —CH$_2$—O—CH$_2$CH$_2$—, —CH$_2$CH$_2$—O—CH$_2$—, and the like.

The term "aryl", as used herein, means aromatic radicals including, but not limited to, phenyl, naphthyl, tetrahydronaphthyl, indanyl, biphenyl and the like.

The term "protecting group", as used herein, means a hydroxy or amino protecting group which is selected from typical hydroxy or amino protecting groups described in Protective Groups in Organic Synthesis edited by T. W. Greene et al. (John Wiley & Sons, 1991).

The term "esters" means a protecting group which can be cleaved in vivo by a biological method such as hydrolysis and forms a free acid or salt thereof. Whether a compound is such a derivative or not can be determined by administering it by intravenous injection to an experimental animal, such as a rat or mouse, and then studying the body fluids of the animal to determine whether or not the compound or a pharmaceutically acceptable salt thereof can be detected.

Preferred examples of groups for an ester of a carboxyl group or a hydroxy group include: (1) aliphatic alkanoyl groups, for example: alkanoyl groups such as the formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl and henicosanoyl groups; halogenated alkylcarbonyl groups such as the chloroacetyl, dichloroacetyl, trichloroacetyl, and trifluoroacetyl groups; alkoxyalkanoyl groups such as the methoxyacetyl group; and unsaturated alkanoyl groups such as the acryloyl, propioloyl, methacryloyl, crotonoyl, isocrotonoyl and (E)-2-methyl-2-butenoyl groups; (2) aromatic alkanoyl groups, for example: arylcarbonyl groups such as the benzoyl, alpha-naphthoyl and beta-naphthoyl groups; halogenated arylcarbonyl groups such as the 2-bromobenzoyl and 4-chlorobenzoyol groups; alkylated arylcarbonyl groups such as the 2,4,6-trimethylbenzoyl and 4-toluoyl groups; alkoxylated arylcarbonyl groups such as the 4-anisoyl group; nitrated arylcarbonyl groups such as the 4-nitrobenzoyl and 2-nitrobenzoyl groups; alkoxycarbonylated arylcarbonyl groups such as the 2-(methoxycarbonyl)benzoyl group; and arylated arylcarbonyl groups such as the 4-phenylbenzoyl group; (3) alkoxycarbonyl groups, for example: alkoxycarbonyl groups such as the methoxycarbonyl, ethoxycarbonyl, propoxycarbonyl, butoxycarbonyl, sec-butoxycarbonyl, t-butoxycarbonyl and isobutoxycarbonyl groups; and halogen- or tri(alkyl)silyl-substituted alkoxycarbonyl groups such as the 2,2,2-trichloroethoxycarbonyl and 2-trimethylsilylethoxycarbonyl groups; (4) tetrahydropyranyl or tetrahydrothiopyranyl groups such as: tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl groups; tetrahydrofuranyl or tetrahydrothiofuranyl groups such as: tetrahydrofuran-2-yl and tetrahydrothiofuran-2-yl groups; (5) silyl groups, for example: tri(alkyl)silyl groups such as the trimethylsilyl, triethylsilyl, isopropyldimethylsilyl, t-butyldimethylsilyl, methyldiisopropylsilyl, methyldi-t-butylsilyl and triisopropylsilyl groups; and silyl groups substituted by one or more aryl and alkyl groups such as the diphenylmethylsilyl, diphenylbutylsilyl, diphenylisopropylsilyl and phenyldiisopropylsilyl groups; (6) alkoxymethyl groups, for example: alkoxymethyl groups such as the methoxymethyl, 1,1-dimethyl-1-methoxymethyl, ethoxymethyl, propoxymethyl, isopropoxymethyl, butoxymethyl and t-butoxymethyl groups; alkoxylated alkoxymethyl groups such as the 2-methoxyethoxymethyl group; and halo(alkoxy)methyl groups such as the 2,2,2-trichloroethoxymethyl and bis(2-chloroethoxy)methyl groups; (7) substituted ethyl groups, for example: alkoxylated ethyl groups such as the 1-ethoxyethyl and 1-(isopropoxy)ethyl groups; and halogenated ethyl groups such as the 2,2,2-trichloroethyl group; (8) aralkyl groups, for example: alkyl groups substituted by from 1 to 3 aryl groups such as the benzyl, alpha-naphthylmethyl, beta-naphthylmethyl, diphenylmethyl, triphenylmethyl, alpha-naphthyldiphenylmethyl and 9-anthrylmethyl groups; alkyl groups substituted by from 1 to 3 substituted aryl groups, where one or more of the aryl groups are substituted by one or more alkyl, alkoxy, nitro, halogen or cyano substituents such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups; alkenyloxycarbonyl groups such as the vinyloxycarbonyl; aryloxycarbonyl groups such as phenoxycaronyl; and aralkyloxy-carbonyl groups in which the aryl ring may be substituted by 1 or 2 alkoxy or nitro groups, such as benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

The term "treating", as used herein, refers to reversing, alleviating, inhibiting, or preventing the onset or the progression of the disorder or condition to which such term applies, or one or more symptoms of such disorder or condition. The term "treatment" as used herein refers to the act of treating, as "treating" is defined immediately above.

Allergy is categorized as follows.

Type I: immediate hypersensitivity is an allergic reaction provoked by reexposure to a specific type of antigen referred to as an allergen Type II: cytotoxic hypersensitivity. The antibodies produced by the immune response bind to antigens on the patient's own cell surfaces in Type II hypersensitivity.

Type III: Immune complex disease. Type III hypersensitivity occurs when antigens and antibodies (IgG or IgM) are present in roughly equal amounts, causing extensive cross-linking.

Type IV: Delayed-type hypersensitivity. Reaction takes two to three days to develop. Unlike the other types, it is not antibody mediated but rather is a type of cell-mediated response.

"Autoimmune diseases" arise from an overactive immune response of the body against substances and tissues normally present in the body. In other words, the body actually attacks its own cells. The immune system mistakes some part of the body as a pathogen and attacks it. Autoimmune diseases include Chagas disease, Chronic obstructive pulmonary disease, Crohn's Disease (one of two types of idiopathic inflammatory bowel disease "IBD"), Dermatomyositis, Diabetes mellitus type 1, Endometriosis, Goodpasture's syndrome, Graves' disease, Guillain-Barre syndrome (GBS), Hashimoto's disease, Hidradenitis suppurativa, Kawasaki disease, IgA nephropathy, Idiopathic thrombocytopenic purpura, Interstitial cystitis, Lupus erythematosus, Mixed Connective Tissue Disease, Morphea, Myasthenia gravis, Narcolepsy, Neuromyotonia, Pemphigus vulgaris, Pernicious anaemia, Psoriasis, Psoriatic Arthritis, Polymyositis, Primary biliary cirrhosis, Rheumatoid arthritis, Schizophrenia, Scleroderma, Sjoegren's syndrome, Stiff person syndrome, Temporal arteritis (also known as "giant cell arteritis"), Ulcerative Colitis (one of two types of idiopathic inflammatory bowel disease "IBD"), Vasculitis, Vitiligo, Wegener's granulomatosis, alopecia areata, celiac disease, Chronic thyroiditis (Hashimoto's thyroiditis), pernicious anemia, autoimmune hepatitis, behcet's disease, uveitis, Atherosclerosis, stroke, Anti-phospholipid antibody syndrome, and the like.

Other features and advantages of the invention will be apparent from the following detailed description and from the claims. While the invention is described in connection with specific embodiments, it will be understood that other changes and modifications that may be practiced are also part of this invention and are also within the scope of the appendant claims. This application is intended to cover any equivalents, variations, uses, or adaptations of the invention that follow, in general, the principles of the invention, including departures from the present disclosure that come within known or customary practice within the art. Additional guidance with respect to making and using nucleic acids and polypeptides is found in standard textbooks of molecular biology, protein science, and immunology (see, e.g., Davis et al., Basic Methods in Molecular Biology, Elsevir Sciences Publishing, Inc., New York, N.Y., 1986; Hames et al., Nucleic Acid Hybridization, IL Press, 1985; Molecular Cloning, Sambrook et al., Current Protocols in Molecular Biology, Eds. Ausubel et al., John Wiley and Sons; Current Protocols in Human Genetics, Eds. Dracopoli et al., John Wiley and Sons; Current Protocols in Protein Science, Eds. John E. Coligan et al., John Wiley and Sons; and Current Protocols in Immunology, Eds. John E. Coligan et al., John Wiley and Sons). All publications mentioned herein are incorporated by reference in their entireties.

The present invention is directed to the use of an EP4 receptor antagonist in the manufacture of a medicament for the treatment of IL-23 mediated diseases.

Therapeutic Methods

Agents identified as EP4 receptor antagonist are administered in a dose effective to treat IL-23 mediated diseases. Such therapeutically effective amounts will be determined using routine optimization techniques that are dependent on the particular condition to be treated, the condition of the patient, the route of administration, the formulation, the judgment of the practitioner, and other factors evident to those skilled in the art in light of this disclosure.

An agent that inhibits EP4 activity can be incorporated into a therapeutic composition. Such EP4 receptor antagonists can include small molecules, nucleic acids, e.g., EP4 antisense nucleic acids, amino acids, peptides, carbohydrates, and anti-EP4 antibodies. Preferably, such agents are combined with a pharmaceutically acceptable delivery vehicle or carrier. Examples of EP4 antibodies include, for example, polyclonal, monoclonal, humanized, anti-idiotypic, chimeric or single chain antibodies, Fab, F(ab')$_2$, and Fab expression library fragments, scFV molecules, and epitope-binding fragments thereof. An antisense oligonucleotide directed to the EP4 gene or mRNA to inhibit its expression is made according to standard techniques (see, e.g., Agrawal et al., Methods in Molecular Biology: Protocols for Oligonucleotides and Analogs, Vol. 20 (1993)).

As used herein, a pharmaceutically acceptable delivery vehicle includes solvents, dispersion media, coatings, antibacterial and antifungal agents, and isotonic and absorption delaying agents that are compatible with pharmaceutical administration. The vehicle may also include other active or inert components, and/or may be targeted to joint tissue by virtue of its composition.

A therapeutic composition is formulated to be compatible with its intended route of administration. Non-limiting examples of routes of administration include parenteral, e.g., intravenous, intradermal, subcutaneous, oral (e.g., by ingestion or inhalation), transdermal (topical), transmucosal, and rectal administration. Solutions or suspensions can be made as described in Remington's Pharmaceutical Sciences, (18th ed., Gennaro, ed., Mack Publishing Co., Easton, Pa., (1990)).

Therapeutic efficacy of such EP4 antagonists can be determined in light of this disclosure by standard therapeutic procedures in cell cultures or experimental animals, e.g., for determining the $ED_{50}$ (the dose therapeutically effective in 50% of the population).

The data obtained from the cell culture assays and animal studies can be used in formulating a range of dosage for use in humans. The dosage may vary depending upon the formulation and the route of administration. For any EP4 antagonist used in the method of the invention, the therapeutically effective dose can be estimated initially from cell culture assays. A dose may be formulated in animal models to achieve a circulating plasma concentration range that includes the $IC_{50}$ as determined in cell culture. Such information can be used to more accurately determine useful doses in humans. Levels in plasma may be measured, for example, by high performance liquid chromatography.

The skilled artisan will appreciate that certain factors may influence the dosage and timing required to effectively treat a mammal including, but not limited to, the severity of the disease or disorder, previous treatments, the general health and/or age of the mammal, and other diseases present. Moreover, treatment of a mammal with a therapeutically effective amount of an EP4 antagonist can include a single treatment or, preferably, can include a series of treatments.

EXAMPLES

Compounds List

3-[2-(4-{2-ethyl-5,7-dimethyl-3H-imidazo[4,5-b]pyridin-3-yl}phenyl)ethyl]-1-[(4-methylbenzene)sulfonyl]urea;

3-[2-(4-{2-ethyl-4,6-dimethyl-1H-imidazo[4,5-c]pyridin-1-yl}phenyl)ethyl]-1-[(4-methylbenzene)sulfonyl]urea (Compound A);

1-{2-[4-(5-acetyl-2-ethyl-1H-1,3-benzodiazol-1-yl)phenyl]ethyl}-3-[(4-methylbenzene)sulfonyl]urea;

3-{2-[4-(2-ethyl-5-methoxy-1H-1,3-benzodiazol-1-yl)phenyl]ethyl}-1-[4-methylbenzene)sulfonyl]urea;

2-{4-[6-chloro-2-ethyl-5-(trifluoromethyl)-1H-1,3-benzodiazol-1-yl]phenyl}ethyl N-[(4-methylbenzene)sulfonyl]carbamate;

3-{2-[4-(6-chloro-5-cyano-2-ethyl-1H-1,3-benzodiazol-1-yl)phenyl]ethyl}-1-[(4-methylbenzene)sulfonyl]urea;

2-(4-{2-ethyl-4,6-dimethyl-1H-imidazo[4,5-c]pyridin-1-yl}phenyl)ethyl N-[(4-methylbenzene)sulfonyl]carbamate;

2-(4-{2-tert-butyl-4,6-dimethyl-1H-imidazo[4,5-c]pyridin-1-yl}phenyl)ethyl N-[(4-methylbenzene)sulfonyl]carbamate;

2-[4-(5-carbamoyl-6-chloro-2-ethyl-1H-1,3-benzodiazol-1-yl)phenyl]ethyl N-[(4-methylbenzene)sulfonyl]carbamate;

1-(2-{4-[2-ethyl-5-(1-hydroxyethyl)-1H-1,3-benzodiazol-1-yl]phenyl}ethyl)-3-[(4-methylbenzene)sulfonyl]urea;

1-(2-{4-[6-chloro-2-(2-hydroxypropan-2-yl)-5-(trifluoromethyl)-1H-1,3-benzodiazol-1-yl]phenyl}ethyl)-3-[(4-methylbenzene)sulfonyl]urea;

2-{4-[6-chloro-2-(pyridin-2-yl)-5-(trifluoromethyl)-1H-1,3-benzodiazol-1-yl]phenyl}ethyl N-[4-methylbenzene)sulfonyl]carbamate;

3-(2-{5-[6-chloro-2-ethyl-5-(trifluoromethyl)-1H-1,3-benzodiazol-1-yl]pyridin-2-yl}ethyl)-1-[(4-methylbenzene)sulfonyl]urea;

2-{4-[6-chloro-2-ethyl-5-(trifluoromethyl)-1H-1,3-benzodiazol-1-yl]phenyl}ethyl N-[(2-chlorobenzene)sulfonyl]carbamate;

3-(2-{4-[5,7-dimethyl-2-(methylamino)-3H-imidazo[4,5-b]pyridin-3-yl]phenyl}ethyl)-1-[(4-methylbenzene)sulfonyl]urea;

4-((1S)-1-{[5-chloro-2-(4-fluorophenoxy)benzoyl]amino}ethyl)benzoic acid;

4-[(1S)-1-({[5-chloro-2-(4-fluorophenoxy)pyridin-3-yl]carbonyl}amino)ethyl]benzoic acid;

4-[(1S)-1-({[5-chloro-2-(3-cyanophenoxy)pyridin-3-yl]carbonyl}amino)ethyl]benzoic acid;

4-[(1S)-1-({[5-chloro-2-(3-fluorophenoxy)pyridin-3-yl]carbonyl}amino)ethyl]benzoic acid (Compound B);

4-[(1S)-1-({[5-chloro-2-(3-chlorophenoxy)pyridin-3-yl]carbonyl}amino)ethyl]benzoic acid;

4-((1S)-1-{[5-chloro-2-(3-fluorophenoxy)benzoyl]amino}ethyl)benzoic acid;

4-((1S)-1-{[5-chloro-2-(3-chlorophenoxy)benzoyl]amino}ethyl)benzoic acid;

4-[(1S)-1-({[5-chloro-2-(2-chloro-4-fluorophenoxy)pyridin-3-yl]carbonyl}amino)ethyl]benzoic acid;

4-[(1S)-1-({[5-chloro-2-(3,4-difluorophenoxy)pyridin-3-yl]carbonyl}amino)ethyl]benzoic acid;

4-[(1S)-1-({[5-chloro-2-(2,3-difluorophenoxy)pyridin-3-yl]carbonyl}amino)ethyl]benzoic acid;

4-((1S)-1-{[5-chloro-2-(2,3-difluorophenoxy)benzoyl]amino}ethyl)benzoic acid;

4-((1S)-1-{[5-chloro-2-(3,4-difluorophenoxy)benzoyl]amino}ethyl)benzoic acid;

4-[(1S)-1-({[5-chloro-2-(3-chloro-5-fluorophenoxy)pyridin-3-yl]carbonyl}amino)ethyl]benzoic acid;

4-[(1S)-1-({5-chloro-2-[(4-chlorophenoxy)methyl]benzoyl}amino)ethyl]benzoic acid;

4-[(1S)-1-({5-chloro-2-[(3-chlorophenoxy)methyl]benzoyl}amino)ethyl]benzoic acid;

4-[(1S)-1-({5-chloro-2-[(4-fluorophenoxy)methyl]benzoyl}amino)ethyl]benzoic acid;

4-[(1S)-1-({5-chloro-2-[(3,4-difluorophenoxy)methyl]benzoyl}amino)ethyl]benzoic acid;

4-[(1S)-1-({5-chloro-2-[(2,4-difluorophenoxy)methyl]benzoyl}amino)ethyl]benzoic acid;

4-{(1S)-1-[({5-chloro-2-[(3-chlorophenoxy)methyl]pyridin-3-yl}carbonyl)amino]ethyl}benzoic acid (Compound C);

4-[(1S)-1-({5-chloro-2-[(3,5-difluorophenoxy)methyl]benzoyl}amino)ethyl]benzoic acid;

4-[(1S)-1-({5-chloro-2-[(3-fluorophenoxy)methyl]benzoyl}amino)ethyl]benzoic acid;

4-{(1S)-1-[({2-[(4-chlorophenoxy)methyl]-5-fluoropyridin-3-yl}carbonyl)amino]ethyl}benzoic acid;

4-{(1S)-1-({5-chloro-2-[(cyclohexylmethoxy)methyl]benzoyl}amino)ethyl}benzoic acid;

4-((4-(5-methoxypyridin-2-yl)phenoxy)methyl)-5-methyl-N-(o-tolylsulfonyl)furan-2-carboxamide (Compound D), 4-{1-[({2,5-dimethyl-4-[4-(trifluoromethyl)benzyl]-3-thienyl}carbonyl)amino]cyclopropyl}benzoic acid (Compound E), 5-chloro-3-[(3-chlorophenyl)methyl]-N-[1-[4-(2H-tetrazol-5-yl)phenyl]ethyl]-2-thiophenecarboxamide, 2,5-dimethyl-N-[(1S)-1-[4-[[(methylsulfonyl)amino]carbonyl]phenyl]ethyl]-4-[[4-(trifluoromethyl)phenyl]methyl]-3-thiophenecarboxamide, 2,5-dimethyl-N-[(1S)-1-[4-[[(phenylsulfonyl)amino]carbonyl]phenyl]ethyl]-4-[[4-(trifluoromethyl)phenyl]methyl]-3-thiophenecarboxamide, 2,5-dimethyl-N-[1-[4-(2H-tetrazol-5-yl)phenyl]cyclopropyl]-4-[[3-(trifluoromethyl)phenyl]methyl]-3-thiophenecarboxamide, 2,5-dimethyl-N-[1-[4-(2H-tetrazol-5-yl)phenyl]cyclopropyl]-4-[[4-(trifluoromethyl)phenyl]methyl]-3-thiophenecarboxamide,
2-chloro-4-[[[[4-[(3-chlorophenyl)methyl]-2,5-dimethyl-3-thienyl]carbonyl]amino]methyl]-benzoic acid,
4-[(1R)-1-[[[2,5-dichloro-4-[(3-chlorophenyl)methyl]-3-thienyl]carbonyl]amino]ethyl]-benzoic acid,
4-[(1S)-1-[[[2,5-dibromo-4-[(3-chlorophenyl)methyl]-3-thienyl]carbonyl]amino]ethyl]-benzoic acid,
4-[(1S)-1-[[[2,5-dichloro-4-(3-chlorobenzoyl)-3-thienyl]carbonyl]amino]ethyl]-benzoic acid,
4-[(1S)-1-[[[2,5-dichloro-4-[(3-chlorophenyl) [(tetrahydro-2H-pyran-2-yl)oxy]methyl]-3-thienyl]carbonyl]amino]ethyl]-benzoic acid,
4-[(1S)-1-[[[2,5-dichloro-4-[(3-chlorophenyl)hydroxymethyl]-3-thienyl]carbonyl]amino]ethyl]-benzoic acid,
4-[(1S)-1-[[[2,5-dichloro-4-[(3-chlorophenyl)methyl]-3-thienyl]carbonyl]amino]ethyl]-benzoic acid,
Methyl 4-[(1S)-1-[[[2,5-dichloro-4-[(3-chlorophenyl)methyl]-3-thienyl]carbonyl]amino]ethyl]-benzoic acid,
4-[(1S)-1-[[[2,5-dichloro-4-[[3-(trifluoromethyl)phenyl]methyl]-3-thienyl]carbonyl]amino]ethyl]-benzoic acid,
4-[(1S)-1-[[[2,5-dimethyl-4-[[3-(trifluoromethyl)phenyl]methyl]-3-thienyl]carbonyl]amino]ethyl]-benzoic acid,
4-[(1S)-1-[[[2,5-dimethyl-4-[[4-(trifluoromethyl)phenyl]methyl]-3-thienyl]carbonyl]amino]ethyl]-benzoic acid,
Methyl 4-[(1S)-1-[[[2,5-dimethyl-4-[[4-(trifluoromethyl)phenyl]methyl]-3-thienyl]carbonyl]amino]ethyl]-benzoic acid,
4-[(1S)-1-[[[2,5-dimethyl-4-[[4-(trifluoromethyl)phenyl]methyl]-3-thienyl]carbonyl]amino]ethyl]-benzoic acid,
4-[(1S)-1-[[[4-[(3-chlorophenyl)methyl]-2,5-dimethyl-3-thienyl]carbonyl]amino]ethyl]-benzoic acid,
4-[(1S)-1-[[[4-[(3-chlorophenyl)methyl]-3-thienyl]carbonyl]amino]ethyl]-benzoic acid,
4-[(1S)-1-[[[4-[(4-chlorophenyl)methyl]-2,5-dimethyl-3-thienyl]carbonyl]amino]ethyl]-benzoic acid,
4-[(1S)-1-[[[5-bromo-4-[(3-chlorophenyl)methyl]-3-thienyl]carbonyl]amino]ethyl]-benzoic acid,
4-[[[[2,5-dichloro-4-[(3-chlorophenyl)methyl]-3-thienyl]carbonyl]amino]methyl]-benzoic acid,
4-[1-[[[2,5-dimethyl-4-[[3-(trifluoromethyl)phenyl]methyl]-3-thienyl]carbonyl]amino]cyclopropyl]-benzoic acid,
4-[1-[[[5-chloro-3-[(3-chlorophenyl)methyl]-2-thienyl]carbonyl]amino]ethyl]-benzoic acid, and Compound A, Compound B, Compound C, Compound D or Compound E is a representative compound in Formula (I), Formula (II), Formula (III), Formula (IV) and Formula (Va, Vb), respectively.

Example 1

IL-23 Production

CD11c dendritic cells (DCs) from the spleens of C57BL/6 mice were purified by auto-magnetic activated cell sorting. The DCs were cultured in a 96-well plate at a density of 6×10⁵ cells per well in the presence of 10 microgram/mL antibody to CD40 for 36 hours. Compounds listed in FIG. 1, that is, Compound A (3-[2-(4-{2-ethyl-4,6-dimethyl-1H-imidazo[4,5-c]pyridin-1-yl}phenyl)ethyl]-1-[(4-methylbenzene)sulfonyl]urea) and Compound B (4-[(1S)-1-({[5-chloro-2-(3-fluorophenoxy)pyridin-3-yl]carbonyl}amino) ethyl]benzoic acid) were added at the beginning of incubation at a dose of 10, 100, or 1000 nM. The supernatant collected at the end of culture was measured by ELISA for IL-23. These results are shown in FIG. 1.

From results of FIG. 1, Compound A and Compound B showed dose-dependent inhibition of IL-23 production in mouse CD11c (+) cells.

The similar inhibition of IL-23 production in mouse CD11c (+) cells is shown in Compound C (4-{(1S)-1-[({5-chloro-2-[(3-chlorophenoxy)methyl]pyridin-3-yl}carbonyl)amino]ethyl}benzoic acid), Compound D (4-((4-(5-methoxypyridin-2-yl)phenoxy)methyl)-5-methyl-N-(o-tolylsulfonyl)furan-2-carboxamide) and Compound E (4-{1-[({2,5-dimethyl-4-[4-(trifluoromethyl)benzyl]-3-thienyl}carbonyl)amino]cyclopropyl}benzoic acid).

The compounds described in the compounds list are similarly conducted in this IL-23 production. The dose-dependent inhibition of IL-23 production in mouse CD11c (+) cells is observed in all cases.

Example 2

DSS Model

Eight weeks-old Balb/c male mice were used in the study. Mice were allocated to four groups; normal control group, disease control group receiving vehicle, and two disease groups receiving different dose of Compound B. Colitis was induced by drinking 2.5% DSS (average molecular weight of 5,000) dissolved in water for 7 days. Compound B in 0.5% methyl cellulose solution (at a dose of 3 or 30 mg/kg) was orally administered for 7 days. The mice were sacrificed on day 11 and the colon was harvested for the evaluation. Colon length, colon weight, and histology score were analyzed. Histology score was determined as follows; 0=no signs of damage; 1=moderate inflammation; 2=severe inflammation. These results are shown in FIG. 2.

Figure 2:
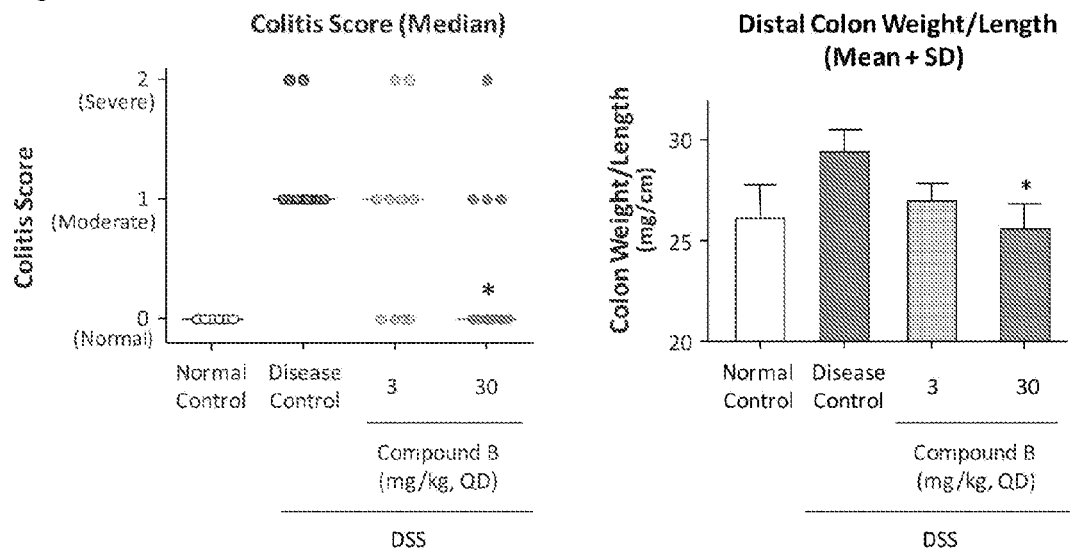
FIG. 2 is a graph showing that Compound B reduces colitis score (left side) and colon weight/length (right side) in a dose-dependent manner.

From results of FIG. 2, Compound B restored colitis score and colon weight/length changes which were induced by DSS in a dose dependent manner. Dose-dependent reduction of colitis score and colon weight/length, are also shown in Compound A, Compound C, Compound D and Compound E.

The compounds described in the compounds list are similarly conducted in DSS model. The dose-dependent inhibition of colitis score and colon weight/length are observed in all cases.

Example 3

Allergic Contact Dermatitis and Psoriasis Model

Eight weeks-old C57BL/6 male mice were used in the study. Mice were sensitized with 0.1 mL of 7% picryl chloride-ethanol on shaved abdominal skin on day O, Seven days later, the mice were treated with 0.02 mL of 1% picryl chloride-olive oil on both sides of the ear by painting. Ear thickness was measured using a thickness gage before the treatment, and 24 and 48 hours after the treatment, and the difference of ear thickness was used as a parameter of ear swelling. Compound B suspended in 0.5% methyl cellulose solution (at a dose of 3 or 30 mg/kg) was administered orally either during the entire experimental period (days 0 to 11) or elicitation (E) period (days 8 to 10). These results are shown in FIG. 3.

From results of FIG. 3, Compound B treated during elicitation (E) period as well as entire period significantly reduced ear swelling in a dose-dependent manner. The maximum efficacy of Compound B was equal to that of prednisolone (Pred) wherein Prednisolone was widely used for allergic contact dermatitis and psoriasis.

The dose-dependent reduction of ear swelling is also shown in Compound A, Compound C, Compound D, and Compound E.

The compounds described in the compounds list are similarly conducted in an allergic contact dermatitis model. The reduction of ear swelling is observed in all cases.

REFERENCE TO FIGS. 1 to 3

(FIG. 1)

Data represent Mean±SD (N=3).

(FIG. 2)

*p<0.05 versus disease control by Mann-Whitney test (N=6–10)

(FIG. 3)

Data represent Mean±SD (N=10).

**p<0.01 versus disease control by Dunnett's test p<0.01 versus disease control by t-test

INDUSTRIAL APPLICABILITY

According to the present invention, a compound of formula (I), (II), (III), (IV), (Va) or (Vb), or a pharmaceutically acceptable salt thereof is useful for the treatment and/or prevention of immune disease or allergy.

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:

1. A method for the treatment of psoriasis in an animal subject including a mammalian subject, by inhibition of IL-23 production, which comprises administering to the animal subject including a mammalian subject, a therapeutically effective amount of the compound, 3-[2-(4-{2-ethyl-4,6-dimethyl-1H-imidazo [4,5-c]pyridin-1-yl}phenyl) ethyl]-1-[(4-methylbenzene)sulfonyl] urea or a pharmaceutically acceptable salt thereof.

* * * * *

UNITED STATES PATENT AND TRADEMARK OFFICE
CERTIFICATE OF CORRECTION

PATENT NO. : 9,457,084 B2  
APPLICATION NO. : 13/580323  
DATED : October 4, 2016  
INVENTOR(S) : Kiyoshi Kanazawa et al.

Page 1 of 1

It is certified that error appears in the above-identified patent and that said Letters Patent is hereby corrected as shown below:

On the Title Page

In Item (60), under "Related U.S. Application Data", in Column 1, Line 1, "61/682,506" should be --61/282,506--

Signed and Sealed this
Twenty-eighth Day of March, 2017

Michelle K. Lee
*Director of the United States Patent and Trademark Office*